US010349625B2

(12) United States Patent
Trottier et al.

(10) Patent No.: US 10,349,625 B2
(45) Date of Patent: Jul. 16, 2019

(54) ANIMAL INTERACTION DEVICE, SYSTEM AND METHOD

(71) Applicant: CLEVERPET, INC, San Diego, CA (US)

(72) Inventors: Leo Trottier, San Diego, CA (US); Daniel Knudsen, San Diego, CA (US)

( * ) Notice: Subject to any disclaimer, the term of this patent is extended or adjusted under 35 U.S.C. 154(b) by 48 days.

(21) Appl. No.: 15/881,656

(22) Filed: Jan. 26, 2018

(65) Prior Publication Data

US 2018/0146641 A1     May 31, 2018

Related U.S. Application Data

(63) Continuation of application No. 14/771,995, filed as application No. PCT/US2014/019927 on Mar. 3, 2014, now abandoned.

(60) Provisional application No. 61/928,939, filed on Jan. 17, 2014, provisional application No. 61/771,161, filed on Mar. 1, 2013.

(51) Int. Cl.
| | |
|---|---|
| *A01K 5/02* | (2006.01) |
| *A01K 15/02* | (2006.01) |
| *A01K 29/00* | (2006.01) |
| *G05B 19/042* | (2006.01) |

(Continued)

(52) U.S. Cl.
CPC .......... *A01K 5/0275* (2013.01); *A01K 5/0114* (2013.01); *A01K 5/02* (2013.01); *A01K 5/0258* (2013.01); *A01K 5/0291* (2013.01); *A01K 15/021* (2013.01); *A01K 15/025* (2013.01); *A01K 29/005* (2013.01); *G05B 19/0428* (2013.01); *G08B 5/22* (2013.01); *G05B 2219/2621* (2013.01)

(58) Field of Classification Search
CPC .... A01K 15/02; A01K 5/0275; A01K 5/0114; A01K 5/0258; A01K 5/0291; A01K 15/021; A01K 5/00; A01K 5/01; A01K 5/02
USPC ........ 340/573.3; 119/51.02, 712, 719, 51.01, 119/720, 721, 908
See application file for complete search history.

(56) References Cited

U.S. PATENT DOCUMENTS

| | | | |
|---|---|---|---|
| 7,424,867 B2 * | 9/2008 | Kates .................. | A01K 15/021 119/719 |
| 8,578,882 B2 * | 11/2013 | Araujo .................... | A01K 5/02 119/51.01 |

(Continued)

*Primary Examiner* — Yvonne R Abbott-Lewis
(74) *Attorney, Agent, or Firm* — Sherrie Flynn; Coleman & Horowitt LLP

(57) ABSTRACT

An animal interaction device is provided that includes a food access component which allows and disallows access to at least a portion of the food. In various embodiments, the allowing and disallowing of access to at least a portion of the food is dependent upon the animal's condition. A method is also provided such that the device above is provided to an animal, one or more indicators are optionally activated, the animal's first condition is sensed via one or more sensors, and based upon the animal's condition, the previously protected food is made accessible, and subsequently the protected food is made available again based upon the animal's second condition. A system is also provided for automatically interacting with an animal including at least one animal interaction device each of which comprises an initial interaction algorithm to automatically interact with the animal. Other aspects of the invention are provided.

20 Claims, 17 Drawing Sheets

Figure 1A:
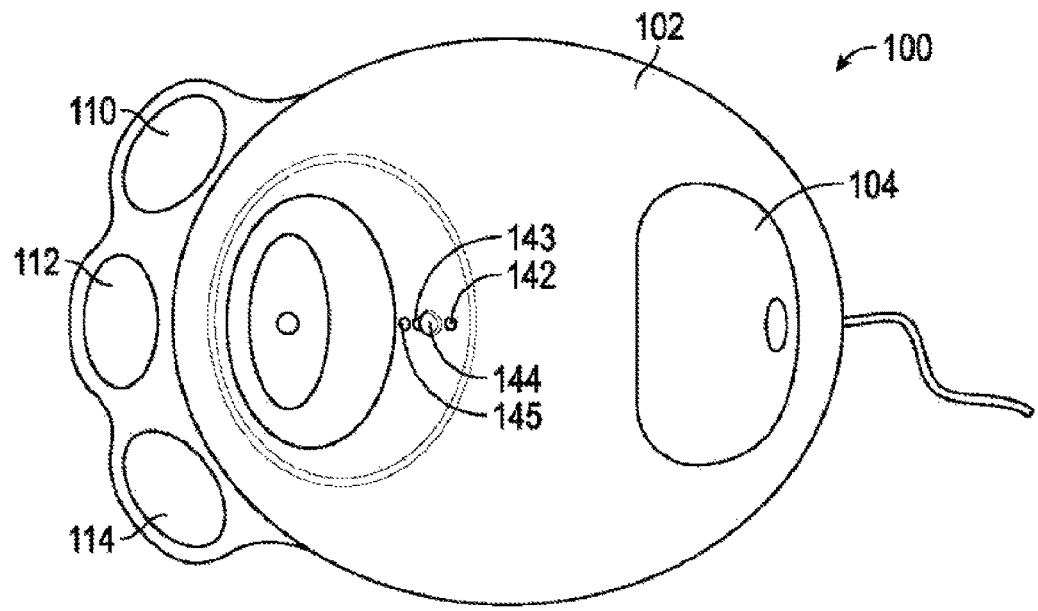

(51) Int. Cl.
*A01K 5/01* (2006.01)
*G08B 5/22* (2006.01)

(56) References Cited

U.S. PATENT DOCUMENTS

| | | | |
|---|---|---|---|
| 8,656,865 B1* | 2/2014 | Foote | A61D 7/00 |
| | | | 119/712 |
| 8,939,111 B2* | 1/2015 | Berntsen | A01K 15/04 |
| | | | 119/721 |
| 8,944,006 B2* | 2/2015 | Anderson | A01K 5/01 |
| | | | 119/51.01 |

* cited by examiner

ANIMAL INTERACTION DEVICE, SYSTEM AND METHOD

CROSS-REFERENCE TO RELATED APPLICATIONS

This application claims priority to U.S. application Ser. No. 14/771,995, filed Sep. 1, 2015, which is a U.S. National Stage of International Application No. PCT/US2014/019927, filed on Mar. 3, 2014, which claims the priority of U.S. Provisional Application No. 61/928,939, filed on Jan. 17, 2014 and U.S. Provisional Application No. 61/771,161, filed on Mar. 1, 2013. The contents of each of the above-referenced applications are incorporated herein by reference in their entireties.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

FIELD

The present teachings relate to devices, systems, methods, and kit for animal interaction.

INTRODUCTION

Captive animals, especially domestic pets, spend thousands of hours each year unattended or in a house alone, often while their owners are off at work. Unlike humans, they have no way to entertain themselves. Nearly every part of an animal enclosure or household—from the size of the door to the height of the light switches to the shapes of the chairs—has been designed to accommodate people. Similarly, entertainment devices in most homes are designed to interact with people, and cannot easily be controlled or accessed by a domestic pet.

There are more than 40 million households in the United States alone that include at least one dog, and more than 35 million that include at least one cat. Many of these animals suffer from boredom daily, and correspondingly, millions of owners feel guilty for leaving their animals alone for hours at a time.

Computer-controlled animal training has existed in a scientific and experimental context for more than 20 years. However, those systems are expensive custom-designed apparatuses that are inappropriate for household use. The training required to configure and operate such systems is generally reserved for the holders of advanced degrees in psychology, neuroscience, and cognitive science. Eliciting particular behaviors from animals takes skill and patience on the part of the experimentalist, and has thus been reserved for research programs aimed at answering questions in about the behavior and its biological underpinnings.

U.S. Pat. No. 8,578,882 describes a system and method for cognitive enrichment of an animal, however because it does not support food removal or describe an ability to provide precise quantities of food, it is inadequate for sustained engagement with domestic pets. While it describes interaction with the "cloud" and the obtaining of data from other devices, this data does not inform the programming of the device in such a way as to impact how the device interacts with an animal. Furthermore, it is not designed in such a way as to be pet-resistant. In addition, the device is restricted to interaction via a visual touch display.

U.S. Pat. No. 7,409,924 describes an entertainment system for animals, but despite the existence of a multi-billion dollar pet products industry in the United States, that system is not commercially available. While this patent alludes to the use of the common techniques of animal training, nowhere in the patent is it described how the automated system could guide an animal from having no interaction with his system to engaging with it without regard for the animal's condition.

Within the prior art it is possible to find many examples of devices that interact with animals by providing positive or negative reinforcement in response to an animal's actions. All of these examples, however, provide only for the possibility of selectively dispensing a treat or portion of food, and are not designed to be able to subsequently prevent access to the treat or food.

Therefore, what is needed is an automated animal interaction device and system that both responds to the animal's condition and can provide precisely controlled reinforcement. There remains a pressing unmet need in the marketplace for a device and system that can automatically, effectively, and affordably engage animals physically and cognitively, without the direct, ongoing interaction of a human.

SUMMARY

The present teachings include an animal interaction device that includes a food access component which allows and disallows access to at least a portion of the food. In various embodiments, the allowing and disallowing of access to at least a portion of the food is dependent upon the animal's condition. In various aspects, the food access is allowed for a predefined time or is allowed for a dynamically determined time. In various aspects, the allowing access occurs at a different time than the disallowing access.

In various aspects, the device above provides the food access component connected to a food container, and a food conveyor connected to the food container, and a presentation platform connected to the food conveyor, wherein the food conveyor is configured to dynamically convey a portion of the food from the container to the presentation platform in relation to the animal's condition, and a controller in electronic communication with the food access component, the food conveyor, the presentation platform, and at least one detector, wherein the controller is configured to control the function of each of the food access component, the food conveyor, the presentation platform, and at least one detector, and further wherein the at least one detector detects the food conveyed from the conveyor onto the presentation platform, and a housing enclosing the food container, food conveyor, and at least a portion of the presentation platform. In various aspects, the presentation platform can be rotatable.

In yet other aspects, the food container contains food. In other aspects, the food is dynamically conveyed according to a predefined algorithm, and in yet other aspects, the predefined algorithm is updatable via the Internet. In another aspect, the device further comprises a transmitter, wherein data related to the function of the device is transmitted electronically to at least one remote computer.

In yet another aspect, the conveyor is a screw conveyor.

In another aspect, the device above is provided, and in the instance the food is in the form of animal kibble, a detector detects the dispensing of an individual piece of kibble or predetermined number of pieces of kibble.

In still another aspect, the device further comprises at least one sensor, and the sensor can be at least one camera. In another aspect, the device further comprises at least one indicator, and the indicator can be at least one speaker or at least one light.

In yet another aspect, data from the at least one sensor is transmitted to the controller. In another aspect, the controller dynamically controls at least one indicator. In another aspect, data provided by the at least one sensor is transmitted to at least one remote computer. In yet another aspect, the controller can be preprogrammed with a predefined algorithm for selectively providing access to the portion of the food and for selectively removing access to the portion of the food. In another aspect, the at least one sensor is used to provide information to the controller about the animal's condition.

In another embodiment, a system is provided for automatically interacting with an animal including at least one animal interaction device each of which comprises an initial interaction algorithm to automatically interact with the animal, the initial interaction algorithm further comprising device instructions selected from the group consisting of (a) presenting stimuli, and (b) continuously or intermittently recording variables selected from the group consisting of the animal condition, the device state, and the time of such recording, and (c) controlling the timing and duration of the presentation of reinforcement selected from the group consisting of positive and negative reinforcement, wherein the intermittent recordings are transmitted to at least one remote computer, and further wherein the at least one remote computer is programmed to modify the initial interaction algorithm informed by the intermittent recordings, and transmit the modified interaction algorithm to the at least one device to replace the initial interaction algorithm.

In various aspects, the animal interaction device provided in the system is the device first described above. In other aspects, the animal interaction includes, but is not limited to, training, modifying the behavior, and modifying the condition of the animal. In yet other aspects, the positive or negative reinforcement is removed from the animal.

In another aspect, data from continuous or intermittent recordings are segregated and inform the modification of the initial or modified interaction algorithm of the at least one animal interaction device. In yet another aspect, the initial interaction algorithm is downloaded upon starting the device. In another aspect, the interaction algorithm is housed on the at least one remote computer, and instructs the at least one animal interaction device to perform the instructions.

In yet another embodiment, a method of animal interaction is provided, including the acts of providing a device first described above to an animal, and optionally activating one or more indicators, and sensing the animal's condition via one or more sensors, and based upon the animal's condition making previously protected food accessible, and subsequently making the food protected again based upon the animal's later condition. In various aspects, the later condition of the animal is the same as the prior condition of the animal.

In another embodiment, a conveyor is provided for controllably conveying particles from a hopper to a staging area a single particle at a time, wherein the particles are non-uniform in size and shape and restricted in diameter to between a range in size X to size 20X. In various aspects, the particles are clumps of food. In yet another aspect, the food particles range in size from 0.2 cm to 4.0 cm.

In another embodiment, a kit is provided which includes the device first described above and instructions for operating the device, both packaged in a box suitable for storage.

In yet another embodiment, the device first described above is provided having a base diameter at least twice the height of the device.

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 1A. Top view of animal interaction device.

Figure 1B:
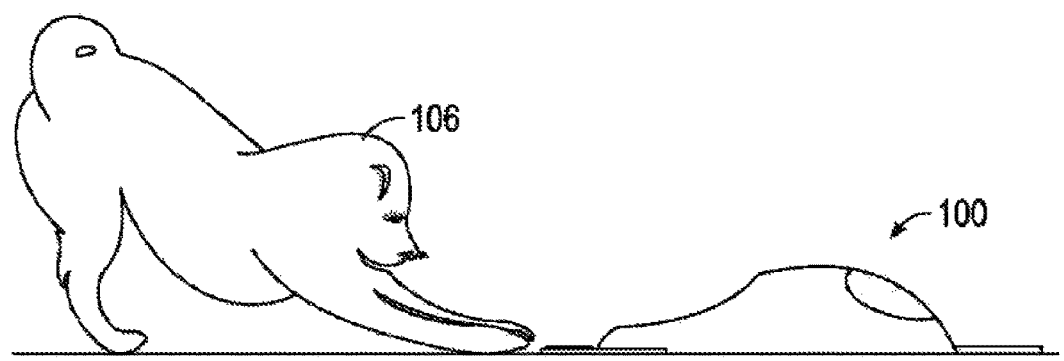

FIG. 1B. Animal interaction device depicted in side view.

Figure 2:
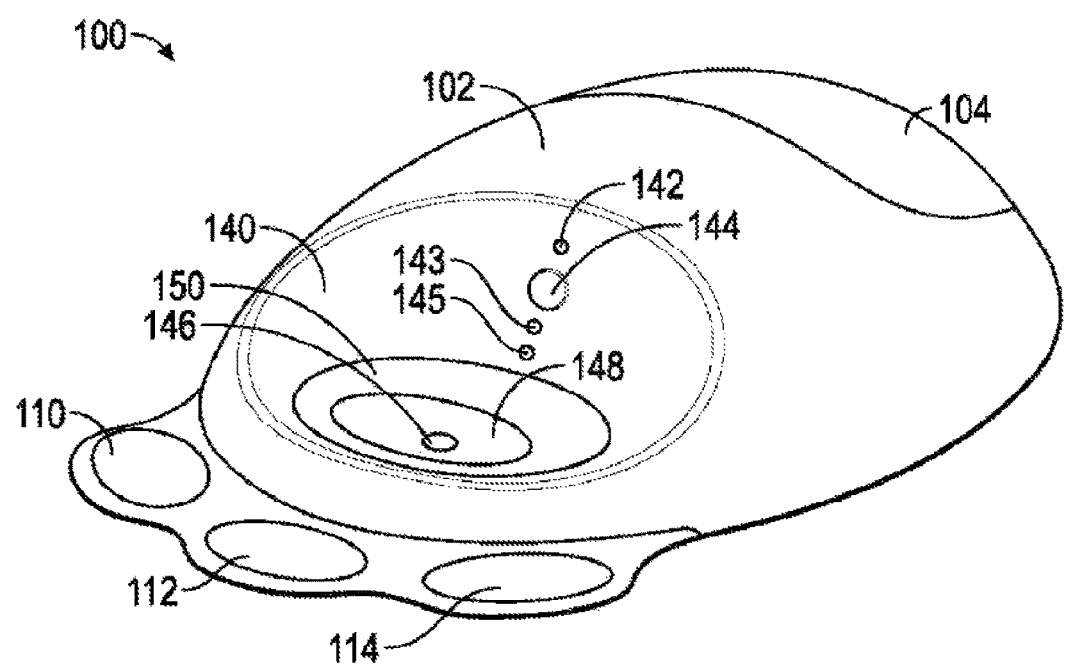

FIG. 2. Perspective view of device.

Figure 3:
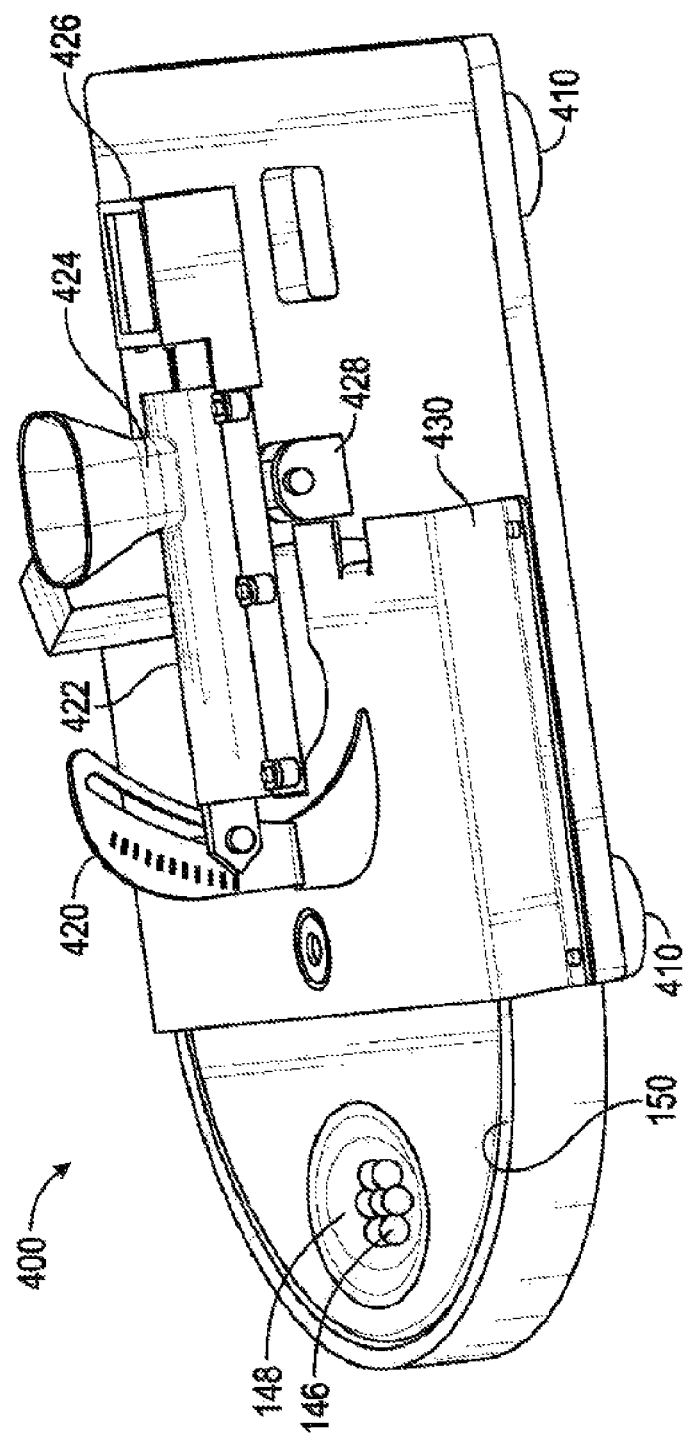

FIG. 3. Internal perspective view of device.

Figure 4:
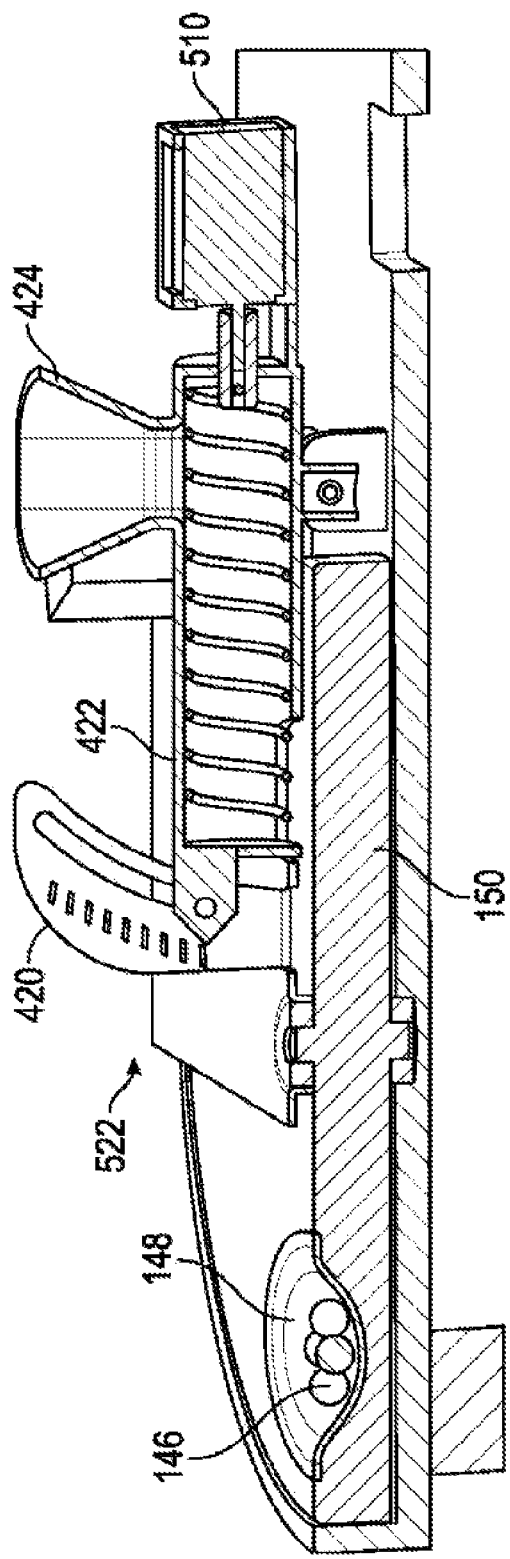

FIG. 4. Internal side view of device.

Figure 5A:
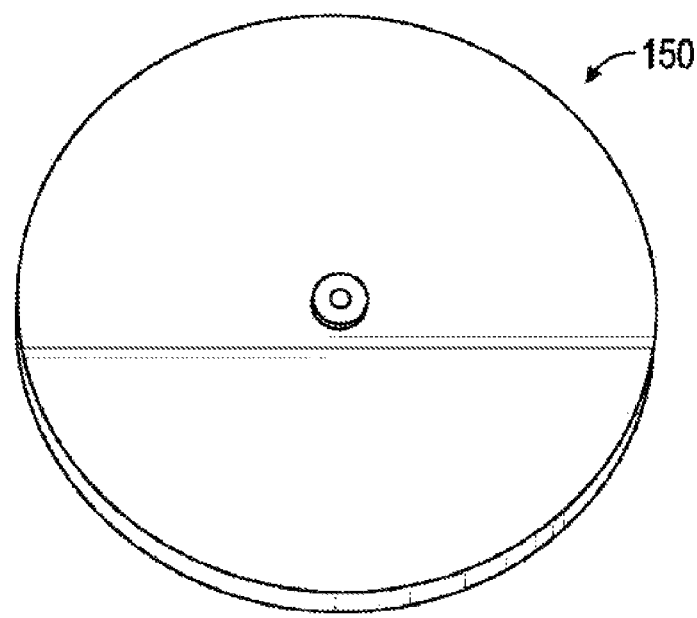

FIG. 5A. Presentation platform, food tray and food bottom view.

Figure 5B:
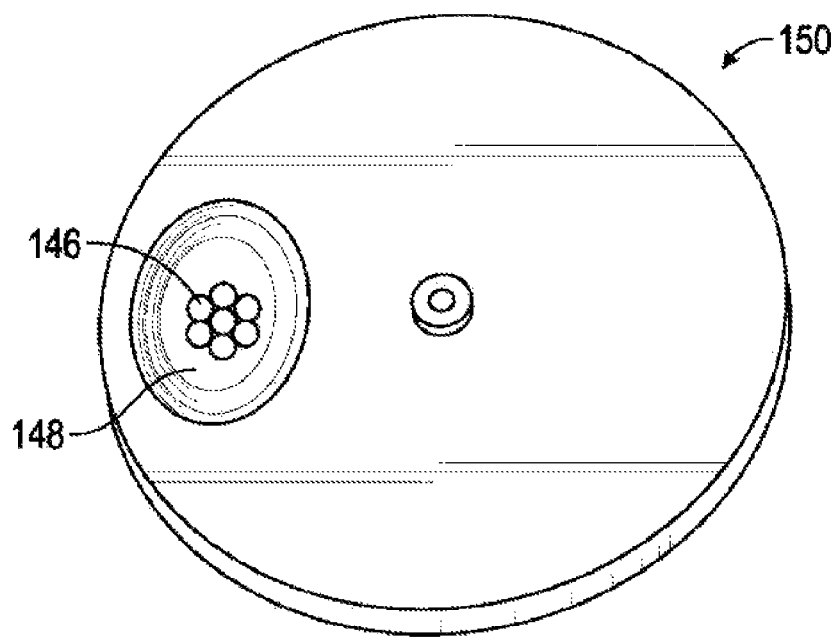

FIG. 5B. Presentation platform, food tray and food top view.

Figure 6:
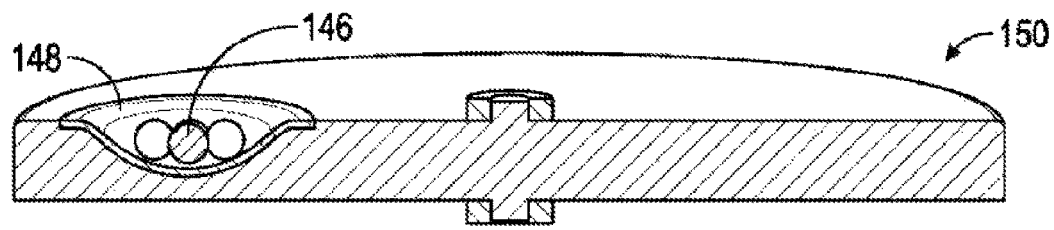

FIG. 6. Presentation platform, food tray and food side view cut out.

Figure 7:
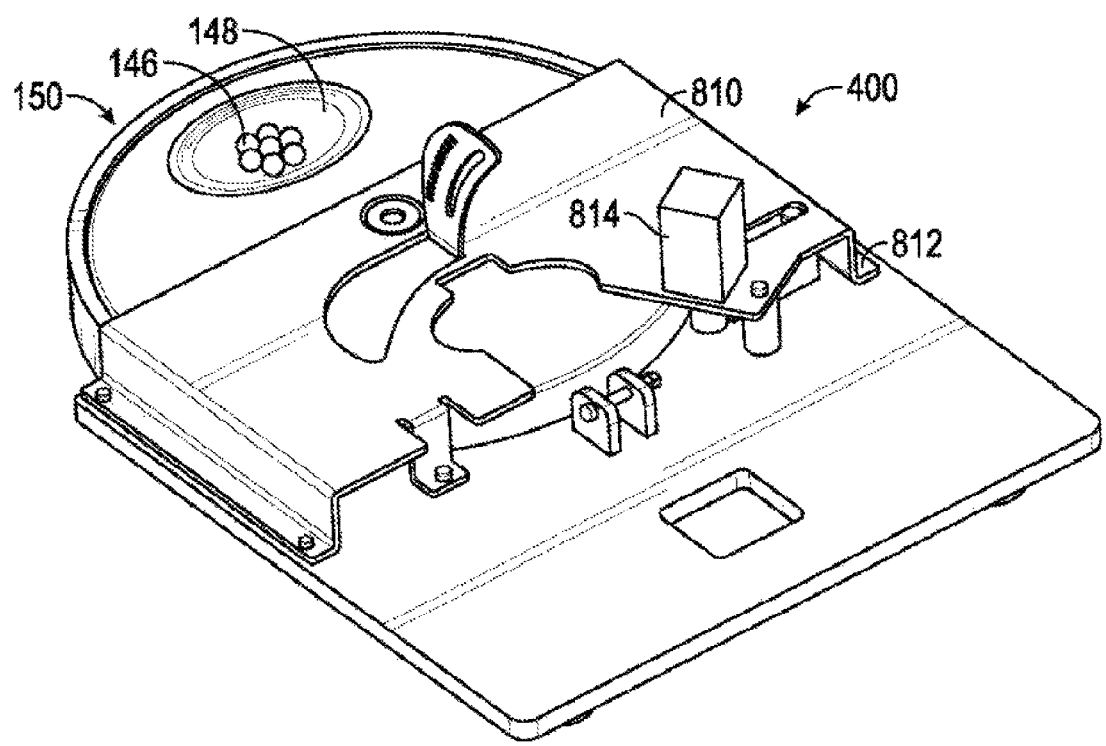

FIG. 7. Presentation platform assembly internal perspective view.

Figure 8:
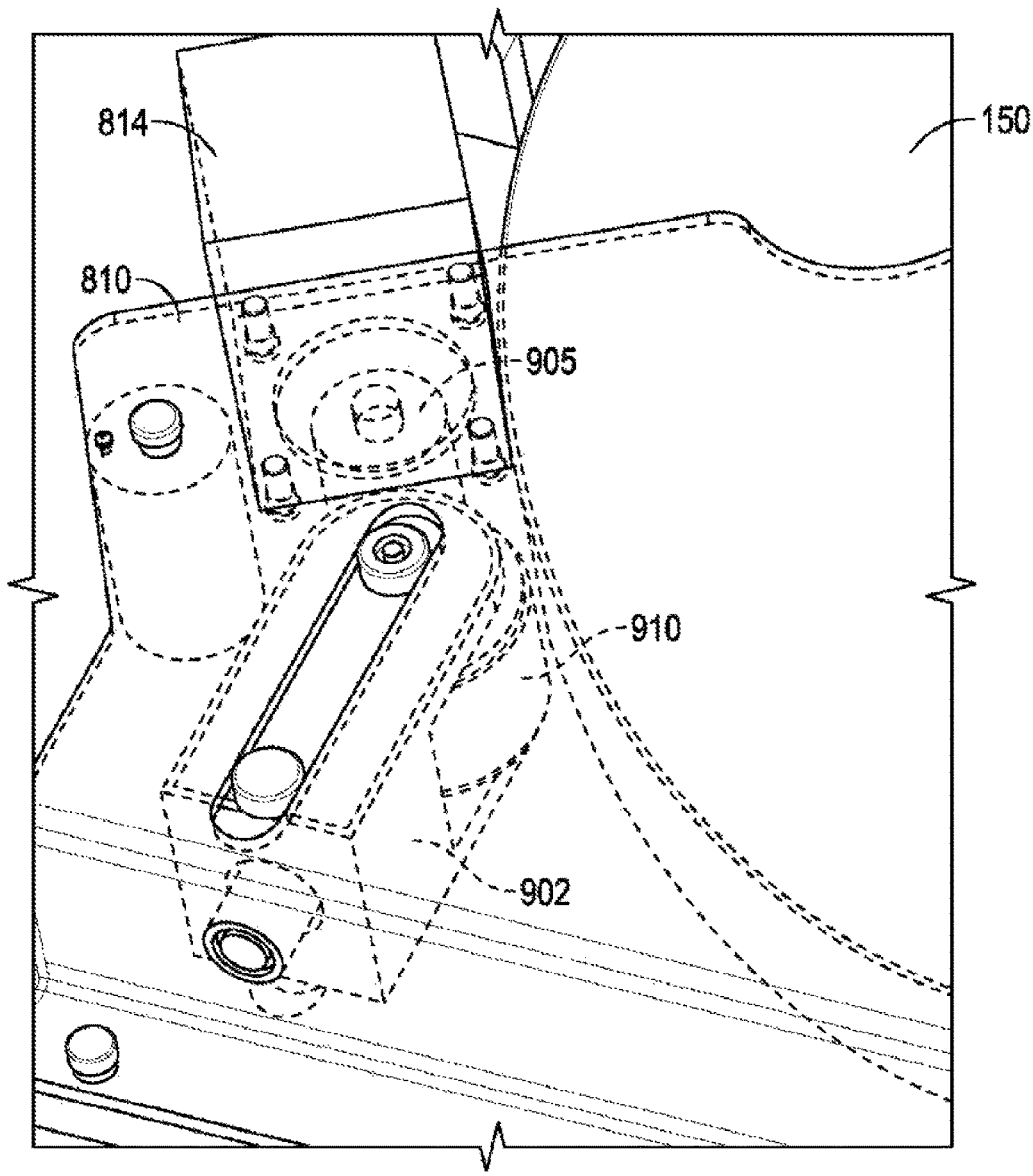

FIG. 8. Blow up of presentation platform friction drive assembly.

Figure 9A:
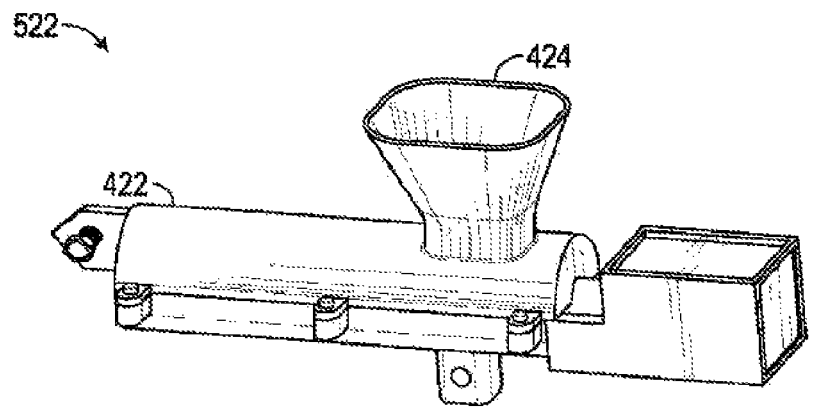

FIG. 9A. Conveyor assembly perspective view.

Figure 9B:
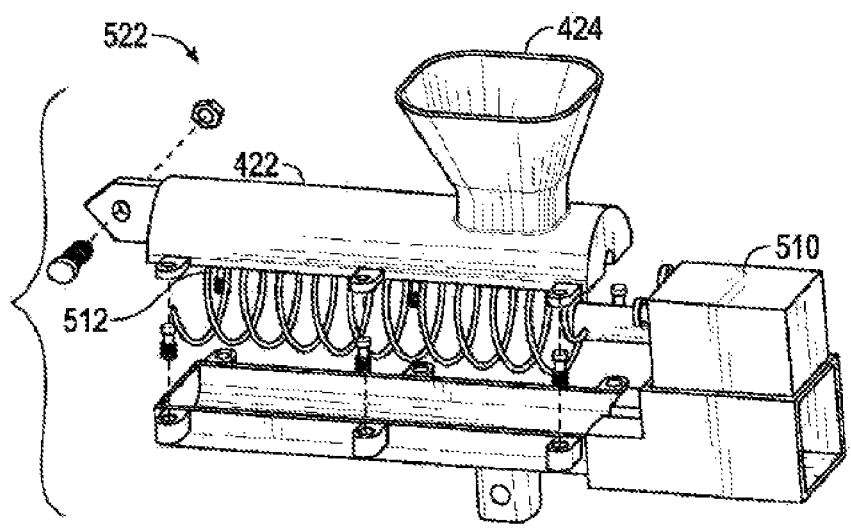

FIG. 9B. Conveyor assembly exploded view.

Figure 10:
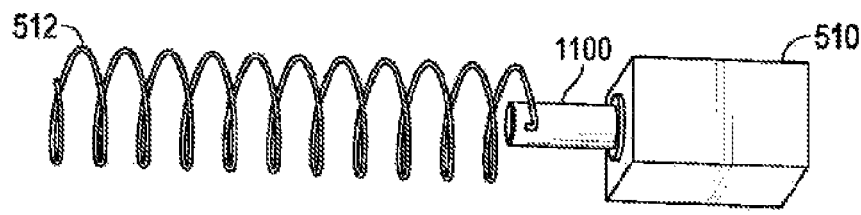

FIG. 10. Internal conveyor assembly including screw conveyor, shaft and motor.

Figure 11A:
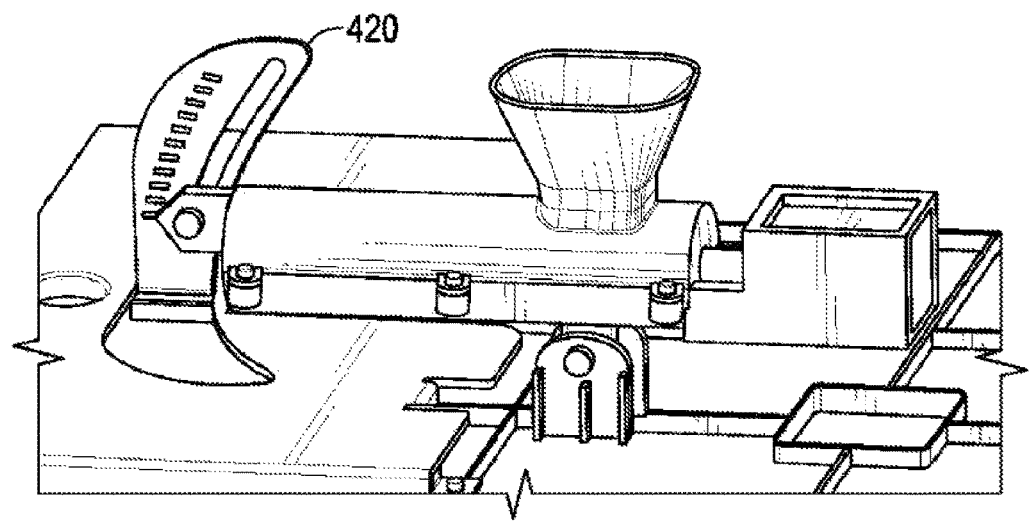

FIG. 11A. Conveyor assembly tilt angle position "A."

Figure 11B:
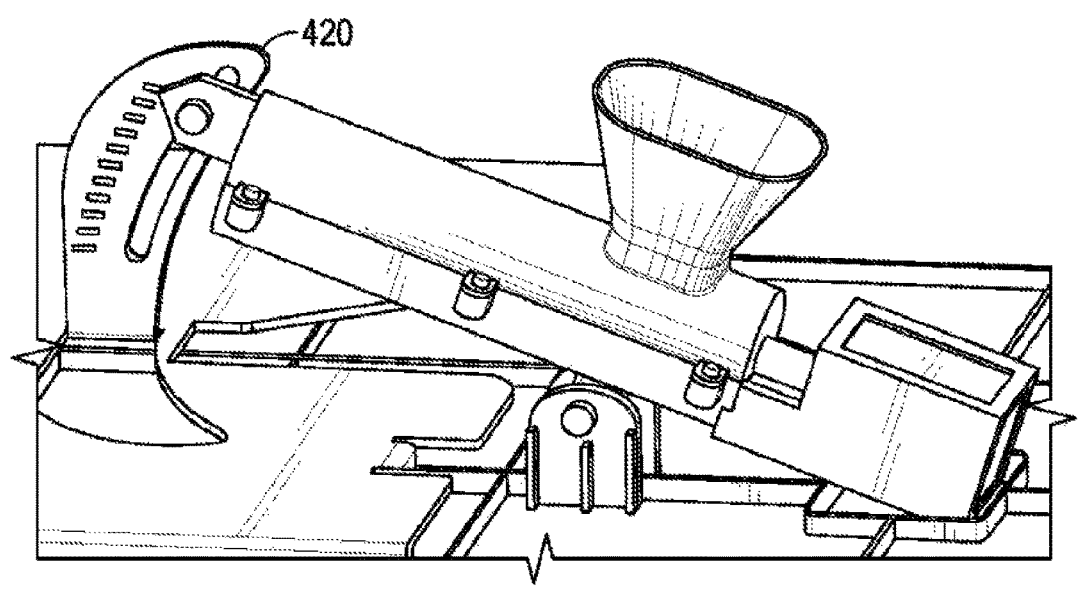

FIG. 11B. Conveyor assembly tilt angle position "B."

Figure 12A:
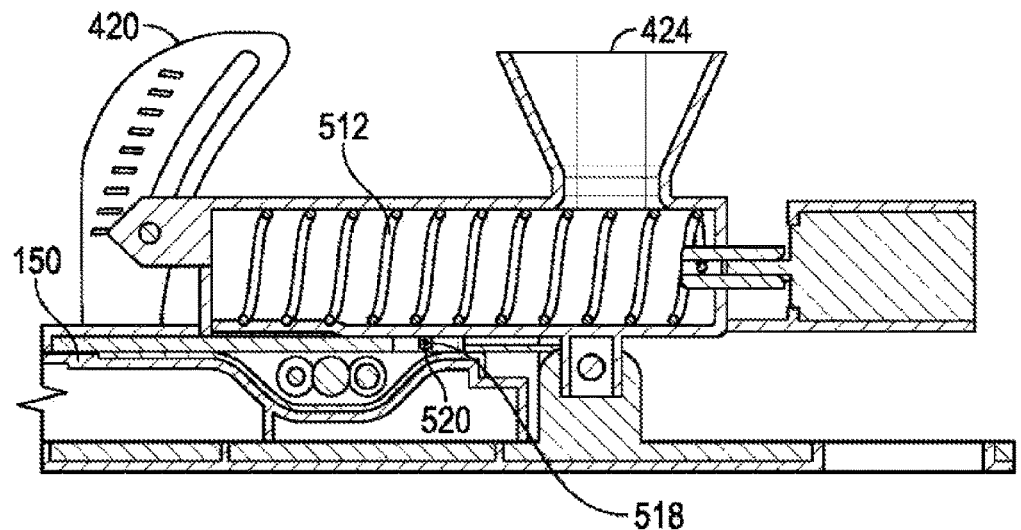

FIG. 12A. Conveyor assembly section view of tilt angle position

Figure 12B:
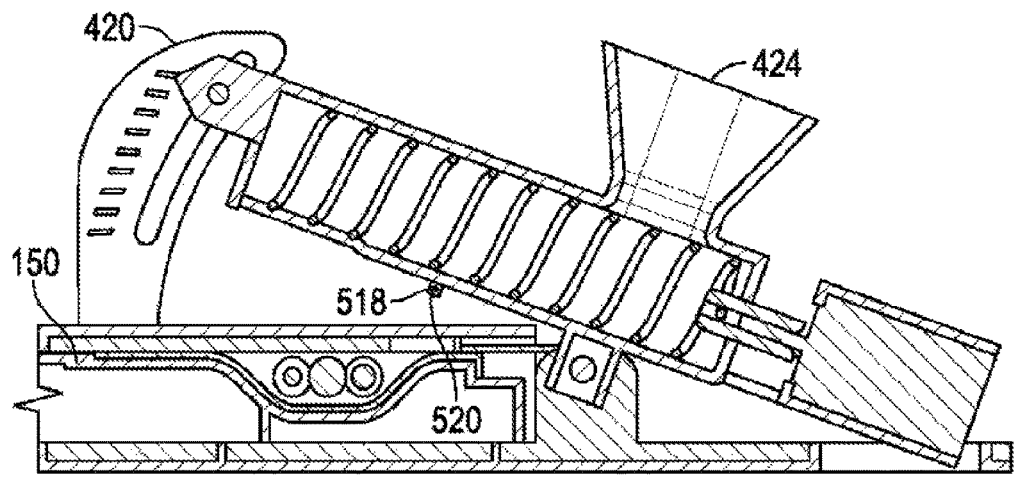

FIG. 12B. Conveyor Assembly section view of tilt angle position

Figure 13:
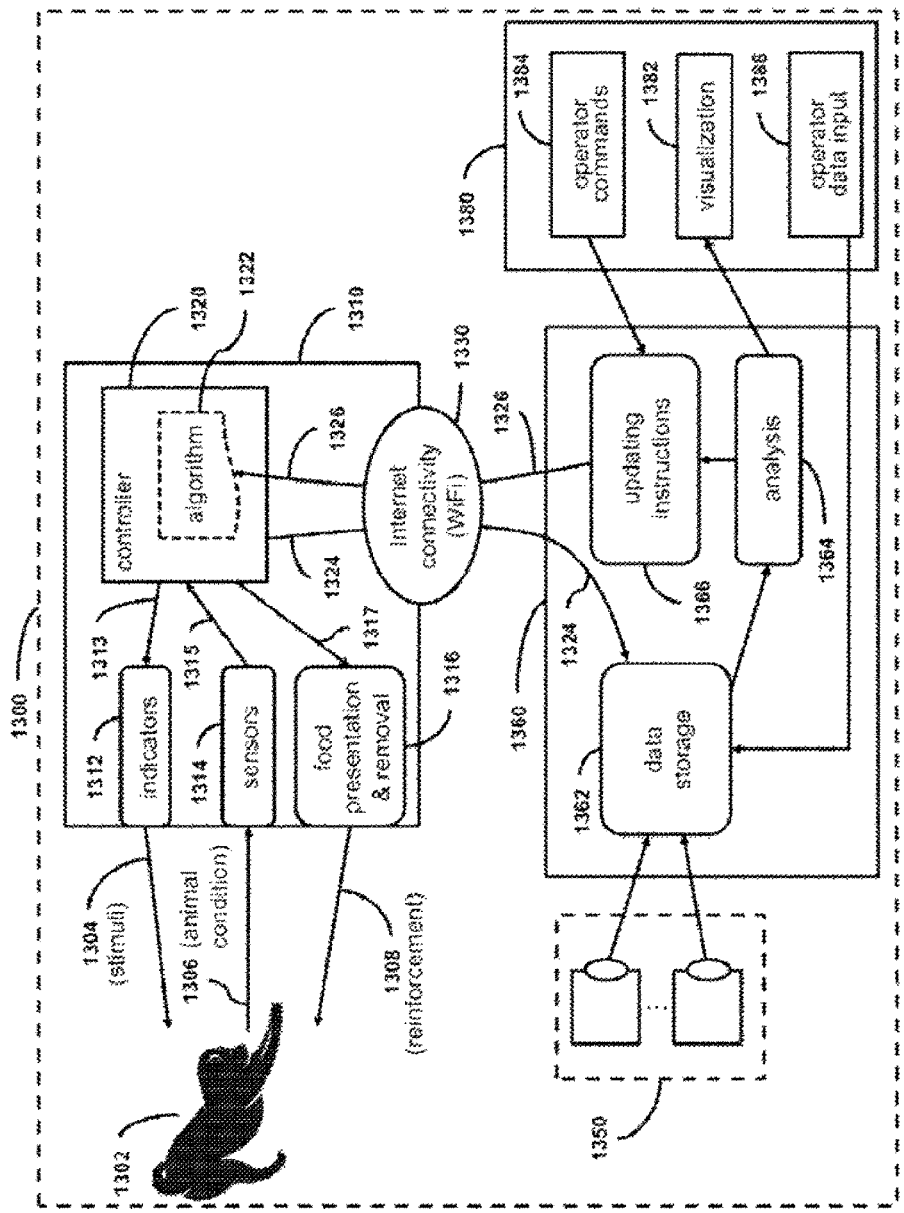

FIG. 13. System for automatically interacting with an animal.

Figure 14:
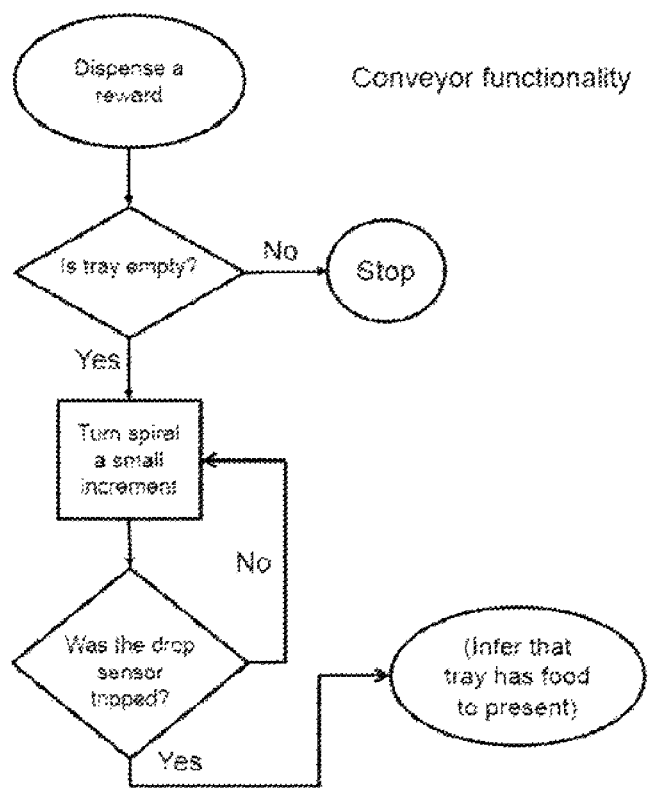

FIG. 14. Conveyor functionality.

Figure 15:
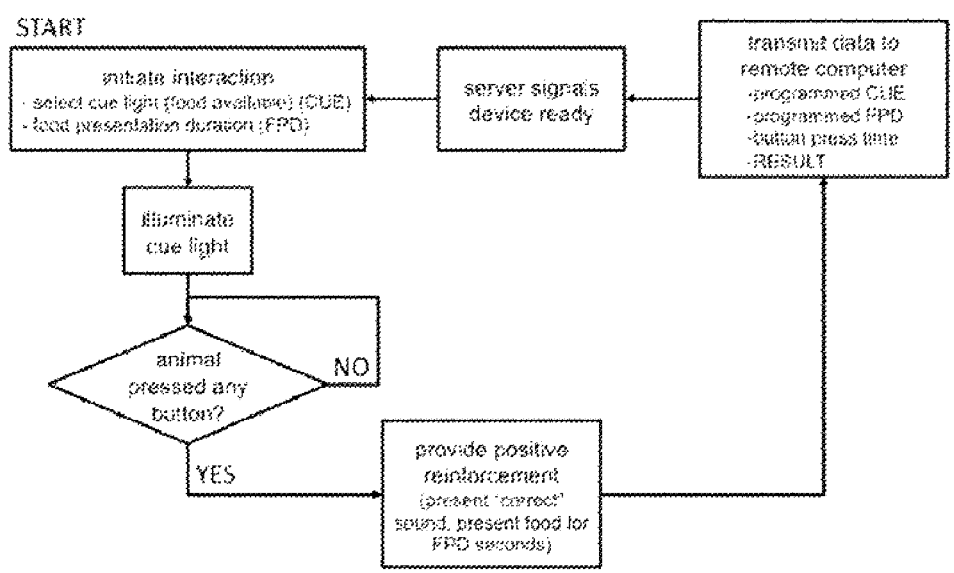

FIG. 15. Animal controls food access directly.

Figure 16:
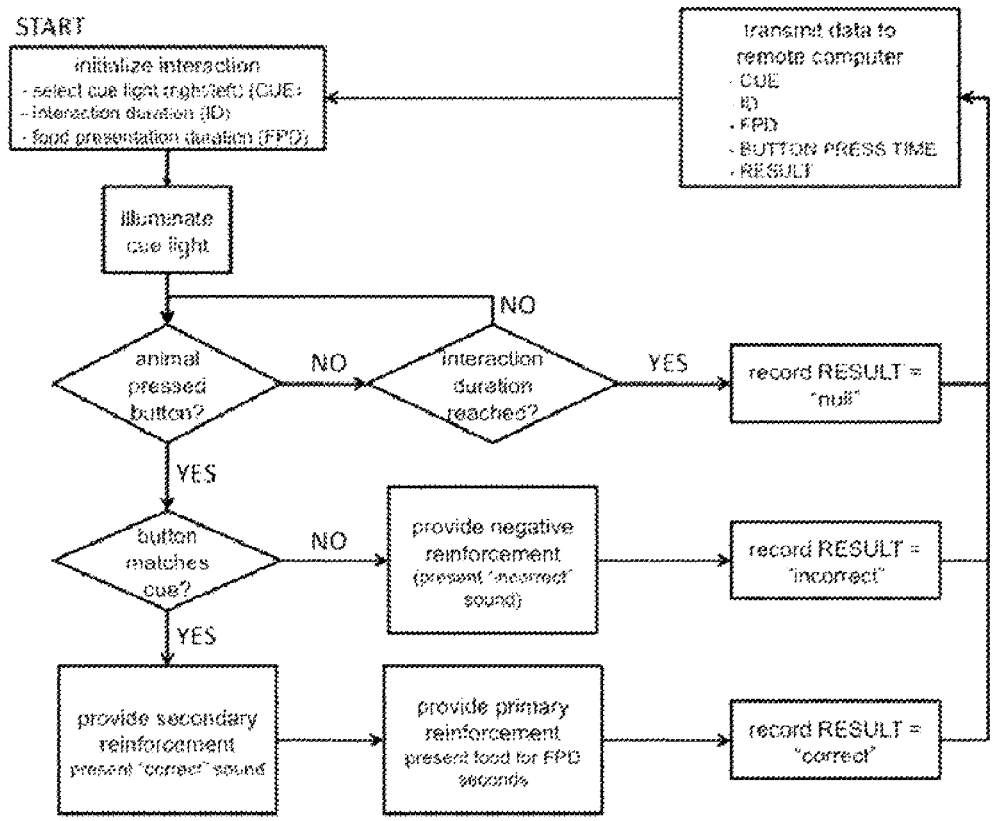

FIG. 16. Cued device interaction.

Figure 17:
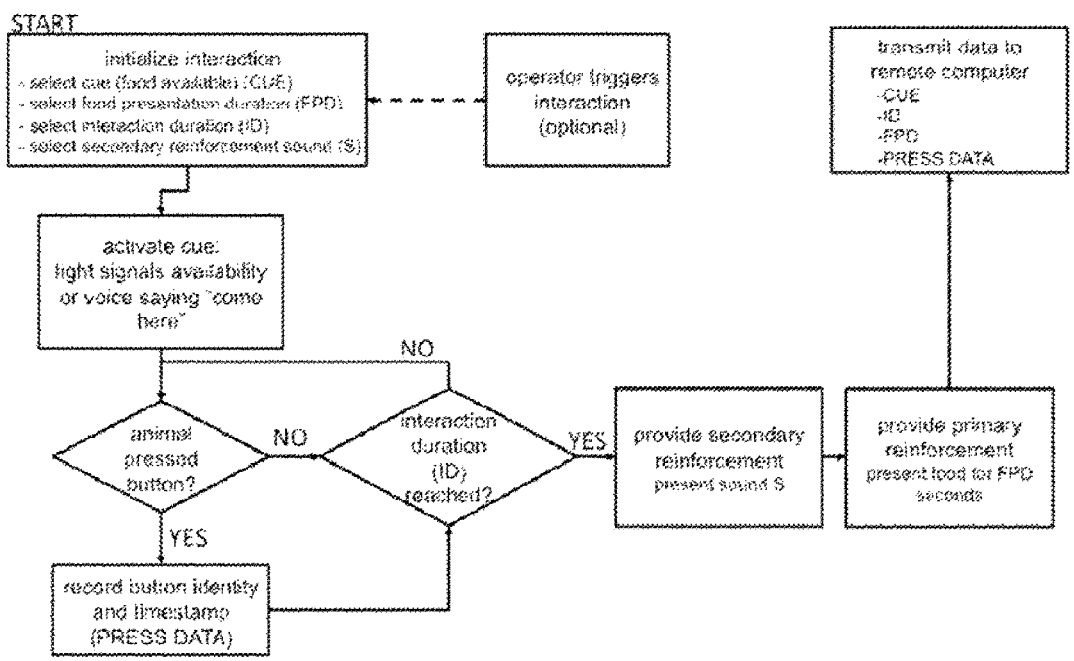

FIG. 17. Slow feeding, Automatic dispensing, Stay close by, Come here.

Figure 18:
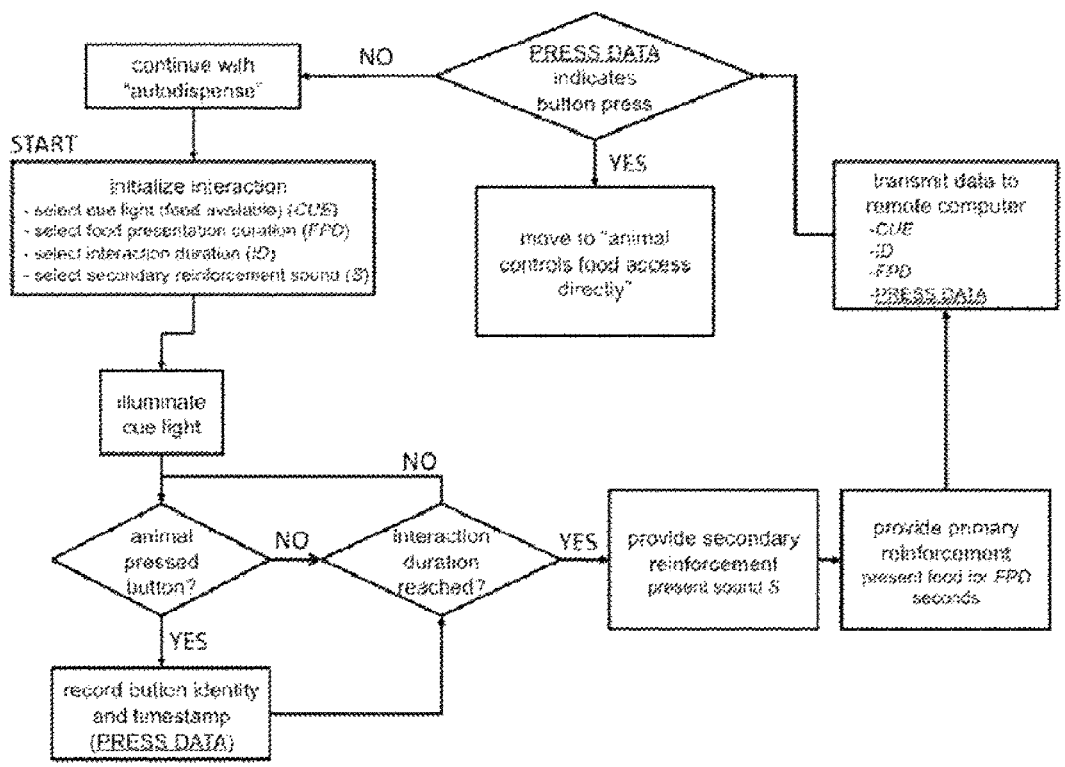

FIG. 18. System automatically moves animal to new interaction regime.

Figure 19:
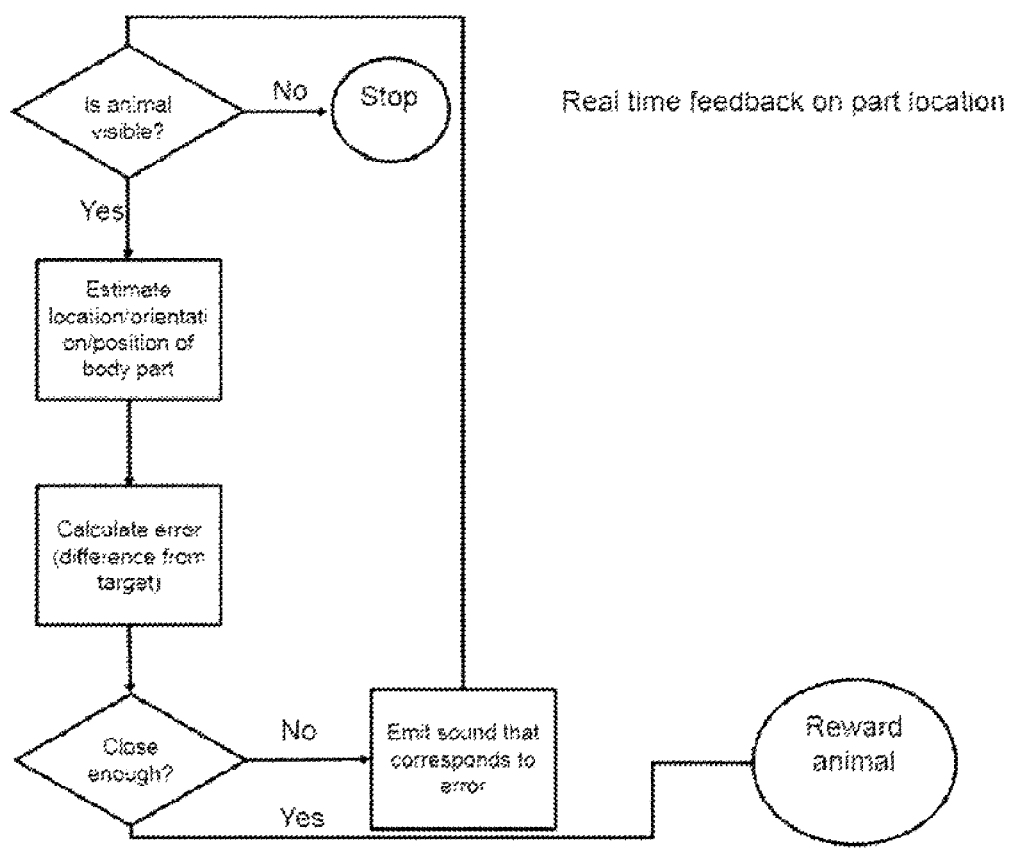

FIG. 19. Real-time animal position cueing.

DETAILED DESCRIPTION

Abbreviations and Definitions

To facilitate understanding of the invention, a number of terms and abbreviations as used herein are defined below as follows:

Animal: As used herein, the term "animal" refers to a eukaryotic organism of the kingdom Animalia. This definition includes, but is not limited to, companion animals such as dogs, cats, birds, and other pets, as well as livestock and working animals such as goats, cows and other animals.

Operator: A person interacting with the device to manipulate certain device features. This definition includes, but is not limited to, a human owner of a pet animal who, for example, sets up the device, loads it with food, and controls and monitors it as described below.

Controller: As used herein, the term "controller" refers to a component of the animal interaction device containing the circuitry to which actuators, detectors, indicators, sensors, and the like are connected. A controller can control the transfer of data from the device to the actuators, detectors, indicators, sensors, other peripheral device, and vice versa, via software programming. Those of skill in the art will recognize that the controller can be a single microchip, a circuit board system, a card, a component of a motherboard, a computer, and a wide variety of other hardware that can control a peripheral device. Such other hardware can include a graphics card, game controller, network interface card, flash memory controller, and the like.

Food: As used herein, "food" refers to (a) one or more pieces of conventional, ostensibly "nutritionally complete" animal food in particle form, or (b) one or more pieces of any animal-edible particle of food (such as a cat or dog "treat" or "kibble").

Accessible: As used herein, the term "accessible" refers to the state of something (e.g. food) being available to non-operators.

Dispense: As used herein, the term "dispense" refers to rendering an amount of something (e.g. food) accessible.

Protected: As used herein, the term "protected" refers to the state of something (e.g. food) being inaccessible to non-operators.

Remove: As used herein, the term "remove" refers to rendering protected an amount of something (e.g. to make protected a portion of food)

Hopper: As used herein, the term "hopper" refers to a protected volume in which food can be stored.

Food tray: As used herein, the term "food tray" refers to the tray from which the animal can eat food.

Presentation platform: As used herein, the term "presentation platform" refers to a platform in which the food tray resides. The presentation platform can be rotatable, and slide in a horizontal direction.

Staging area: As used herein, the term "staging area" refers to a protected volume in which food can reside and from which the food can be made accessible.

Conveyor: As used herein, the term "conveyor" refers to component of the animal interaction device by which food is transported from the hopper to the food tray. The conveyor can be completely integrated into the device or a removable unit.

Conveyor channel: As used herein, the term "conveyor channel" refers to the space in which the conveyor is located and through which passes the food.

Hopper end: As used herein, the term "hopper end" refers to the aspect of the conveyor that is in communication with the hopper, by which food enters the conveyor channel.

Delivery end: As used herein, the term "delivery end" refers to the aspect of the conveyor that delivers the food (that had passed through the conveyor channel) to the food tray.

Delivery area: As used herein, the term "delivery area" refers to the protected volume residing within the staging area in which food from the delivery end is communicated to the food tray.

Reception mode: As used herein, the term "reception mode" refers to a state of the presentation platform in which the food tray is arranged in the delivery area so as to be able to receive food.

Inspection mode: As used herein, the term "inspection mode" refers to a state of the presentation platform during which the food tray may be inspected to determine whether it contains food.

Presentation area: As used herein, the term "presentation area" refers to the unprotected volume to which the food tray can move in order to make accessible any food within the food tray.

Presentation mode: As used herein, the term "presentation mode" refers to the state of the presentation platform in which the food tray is in the presentation area and made accessible.

Ready mode: As used herein, the term "ready mode" refers to the state of the presentation platform wherein food is known to be in the food tray and the device is ready to switch to presentation mode on demand.

Detector: As used herein, the term "detector" refers to a component that detects the presence, absence, or location of food.

Animal condition: As used herein, the term "animal condition" or "animal's condition" is broadly defined to include any behavior, movement, postural position, change in postural position, or any physiological or physical characteristics or change in physiological or physical characteristics of an animal.

Animal condition may reflect the state of the animal with respect to its physical characteristics, for example the animal's location (or the location or change in location of a particular part or parts of the animal) with respect to a defined space, the animal's orientation (or the orientation or change in orientation of a particular part or parts of the animal) in that space, likewise its position or its orientation (or the position or orientation or change in position or orientation of a particular part or parts of the animal) relative to a specific object, for example, pressing a button (with a paw or nose), pressing a lever, touching a touchpad, licking a lickometer, rolling a wheel or ball, flipping a switch.

Animal condition may refer to the posture or change in posture of the animal, including movement of the whole or part or parts of the animal. Some examples include: sitting, standing, walking, running (including different types of gaits), turning, laying down, laying on stomach, lying on side, lying on back, standing on two legs, standing on four legs, holding one paw up, pressing a button, touching a touchpad, moving a lever, holding tail up, holding tail down, wagging tail. Animal condition also includes facial postures or changes in facial posture, including the position and movement of the mouth, lips, tongue, ears, eyes, eyelids, eyebrows, cheeks, nose, or whiskers.

Animal condition may also refer to physiological characteristics or changes in physiological characteristics such as level of satiation or hunger, level of thirst, the need to urinate or defecate, temperature, rate of breathing, level of certain compounds in the bloodstream, lymph, ocular fluids (tears), or cerebrospinal fluid, the physiological activity of the nervous system or a part or parts of the nervous system. Animal condition may also refer broadly to the physiological characteristics of the animal with respect to health or sickness.

Animal condition may also include inferred affective characteristics, for example: level of arousal or excitement, level of interest, boredom, happiness, sadness, frustration, anger, level of motivation, humor, jealousy, shame, guilt.

Animal condition may also be a combination of one or more of the abovementioned types of characteristics, and may be describable by a commonly recognized behavior such as: wagging its tail, turning, moving in a particular direction by, for example, running or walking or rolling or sliding, chasing its tail. The behaviors may be vocalizations or audible behaviors, for example: barking, singing, whining, crying, growling, purring, sniffing, breathing, coughing, sneezing. The behaviors may be finer movements, for example, chewing, biting, licking, sniffing, turning head, tilting head. The behaviors might be linked in some way to the animal's physiology, for example: urinating, defecating, shedding fur or hair, scratching, scraping, rubbing, or grooming.

The animal's condition may also refer to something that is sensed directly by sensors, deduced by combinations of information from one or more sensors, or it may be inferred via information from zero or more sensors using indirect methods. For example, if it was known that the animal had last eaten at a particular time, say 8 AM, then it might be inferred that the animal would be less satiated at 4 PM than it was at 9 AM.

Sensor: As used herein, the term "sensor" is broadly defined to include any component configured to sense or infer an animal's condition.

Stimulus: As used herein, the term "stimulus" (plural: "stimuli") is broadly defined to include any visual, auditory, tactile, haptic, olfactory, or gustatory information that can be perceived by an animal, or any other sensation that can be perceived by an animal.

Indicator: As used herein, the term "indicator" is broadly defined to include any component that can produce a stimulus or stimuli.

Actuator: As used herein, the term "actuator" is broadly defined to include any component of the device that can cause the movement of itself or any other component (e.g., a motor).

Animal Interaction Device, System, and Methods

The present invention is directed to devices, systems, and methods designed to interact with at least one animal. A device is provided for interacting with an animal and can operate, for example, via one or more indicators, via one or more sensors, and via presenting a food reward for a limited amount of time. A system is provided which includes such a device and can also function, for example, connected to remote computers via the internet that can store data from the device and other devices and update the way the device interacts with at least one animal based on the data, and optionally based on input from an operator (such as the owner of the animal). Furthermore, a method is described which uses the system and the device, for example, to automatically interact with an animal. Other embodiments of the present invention are provided herein.

Positive and Negative Reinforcement

Prior devices are designed to present stimuli to an animal, but do not respond to an animal's condition, for example, through positive or negative reinforcement. There are several problems associated with this. If an animal performs a desired behavior or satisfies a desired condition, and then is presented with reinforcement (e.g., some food), but does not avail itself of this reinforcement quickly enough, then the provision of reinforcement failed to accomplish its goal, and, worse, the provided reinforcement could even constitute reinforcement for some behavior or condition that was expressed in the time between the initial presentation of the reinforcement and the consumption of the reinforcement (eating, in the case of a food reinforcement). In other words, reinforcement must be in close temporal proximity to the behavior or condition one desires to reinforce, and though it must come after this behavior or condition, it cannot last indefinitely.

Key to shaping an animal's behavior is reliably following desired behaviors with positive reinforcement. The extent to which a particular behavior performed by the animal predicts a future reward determines the extent to which that behavior will increase in frequency in the future (relative to other behaviors). This is another manner in which the duration of reinforcement presentation is essential: if the animal performs desired behavior X and is reinforced with the presentation of food immediately afterward (so that the behavior can be the to predict the reinforcement), it will be more likely to perform behavior X in the future as opposed to say behavior Y. However, if the reinforcement is presented to the animal for a long enough time that it is able to perform both behaviors X and Y before it is provided the reinforcement (e.g. food), the reinforcement will be attributed to both behaviors X and Y, instead of just the desired behavior, X, and the animal will be more likely to perform both behaviors X and Y in the future.

The present invention overcomes the problems associated with previous devices, and the temporal specificity afforded by the present device, system, and method ensure that the animal associates the reward with a particular desired behavior or condition.

Animal Interaction Device

The device is controlled by a controller and can be connected to a number of sensors and indicators with which an animal interacts. The device also comprises a container for holding food. Such food is normally protected (difficult for animals to access) and portions of food are controllably made accessible to an animal. The device's operation includes the ability to remove food after it is presented. Examples 1-9 provide non-limiting examples of the device and its operation.

Accordingly, the present invention provides an animal interaction device that includes a food access component which allows and disallows access to at least a portion of the food. In various embodiments, the allowing and disallowing of access to at least a portion of the food is dependent upon the animal's condition. In various aspects, the food access is allowed for a predefined time or is allowed for a dynamically determined time. The term "dynamically" as used herein means that the function described is not static or unchangeable. For example, dynamically conveying a portion of food can be done in response to the animal's condition rather than at regular, predetermined time intervals. In various other aspects, the allowing access occurs at a different time than the disallowing access.

In various aspects of the present invention, the device above provides the food access component connected to a food container, and a food conveyor connected to the food container, and a presentation platform connected to the food conveyor, wherein the food conveyor is configured to convey a portion of the food from the container to the presentation platform in relation to the animal's condition, and a controller in electronic communication with the food access component, the food conveyor, the presentation platform, and at least one detector, wherein the controller is configured to control the function of each of the food access component, the food conveyor, the presentation platform, and at least one detector, and further wherein the at least one detector detects the food conveyed from the conveyor onto the presentation platform, and a housing enclosing the food container, food conveyor, and at least a portion of the presentation platform. In various aspects, the presentation platform can be rotatable. In various aspects, the food conveyor can provide the food dynamically. The food access component, the food conveyor, the presentation platform, and at least one detector are described more fully herein. The housing can be made of any suitable material, and those of skill in the art will recognize various materials which can be used to form the enclosure, including various plastics and metals.

In yet another aspect, a rotatable presentation platform is connected to the food conveyor, wherein the food conveyor is configured to dynamically convey a portion of the food from the container to the presentation platform in relation to the animal's condition.

In yet other aspects, the food container contains food. In other aspects, the food is dynamically conveyed according to a predefined algorithm, and in yet other aspects, the predefined algorithm is updatable via the Internet. In another aspect, the device further comprises a transmitter, wherein data related to the function of the device is transmitted electronically to at least one remote computer. Those of skill in the art will understand that various transmitters can be used with a variety of receivers to communicate data between devices, components, and units of the present invention. The device can interact with one or more remote computers to implement certain commands in the controller, as well as update such controller commands. The updating can further be implemented using the system described below.

In yet other aspects, the food container contains food. In other aspects, the food is dynamically conveyed according to a predefined algorithm, and in yet other aspects, the predefined algorithm is updatable via the Internet. In another aspect, the device further comprises a transmitter, wherein data related to the function of the device is transmitted electronically to at least one remote computer.

In yet another aspect, the conveyor is a screw conveyor.

In another aspect, the device above is provided, and in the instance the food is in the form of animal kibble, a detector detects the dispensing of an individual piece of kibble or predetermined number of pieces of kibble.

In still another aspect, the device further comprises at least one sensor, and the sensor can be at least one camera. In another aspect, the device further comprises at least one indicator, and the indicator can be at least one speaker or at least one light.

In yet another aspect, data from the at least one sensor is transmitted to the controller. In another aspect, the controller dynamically controls at least one indicator. In another aspect, data provided by the at least one sensor is transmitted to at least one remote computer. In yet another aspect, the controller can be preprogrammed with a predefined algorithm for selectively providing access to the portion of the food and for selectively removing access to the portion of the food. In another aspect, the at least one sensor is used to provide information to the controller about the animal's condition.

As depicted in FIGS. 1A and 1B, device 100 comprises housing 102 and hopper cover 104. A variety of interactive sensors and indicators 110, 112, 114, 142, 143, 144, and 145 are depicted, although any number of interactive indicators may be provided for interacting with animal 106. Such sensors and indicators will be discussed in full infra.

As depicted in FIG. 2, device 100 further comprises a presentation area 140 which includes sensors 110, 112, 114, 142, 144, food tray 148, presentation platform 150, and indicators, 110, 112, 114, 143, 145 (110, 112, 114 are assemblies which comprise both a sensor and an indicator, described below). Animal food may be provided to food tray 148 and is shown in this FIG. 2 as 146. In one configuration, sensors 142 and 144 can be a microphone and camera, respectively. In one configuration, sensors 110, 112, and 114 can be touch-based digital buttons. In one configuration, indicators 110, 112, 114, and 145 can be programmably illuminable multicolored lights. In one configuration, indicator 143 can be a speaker.

Hopper

The device comprises a food container in which food can be placed. The volume of the hopper can vary according to the configuration of the device and the animal with which the device is interacting. In one instance, if the animal is of a large species, such as an elephant, the hopper can have a volume commensurate with the daily amount of food intake including 500 L, 400 L, 300 L, 200 L, 100 L, and other volumes. In another instance, for less large animals, the range of food can range from about 5 mL to 20 L, and in various aspects 10 mL to 10 L, and in various aspects 20 mL to 5 L, and in yet other aspects 50 mL to 1 L. The enclosure of the hopper is designed such that it cannot be opened by an animal, but can be opened by an operator as necessary.

The volume is designed such that it directs the food to a conveyor that then carries the food away from the hopper towards the food tray contained in the presentation platform. In one configuration, the conveyor can be configured with respect to the hopper to create a slope downward toward the bottom of the conveyor.

In various aspects, the hopper can include additional features, such as 1) a volumetric measurement along the inside of the hopper, 2) a transparent vertical line along the side of the hopper to enable operators to see the volume of food remaining within the hopper, and 3) a scale for weighing the contents of the hopper, or other method of electronically determining the volume of food within the hopper.

The hopper may be configured within the device to be removable by the operator to allow for easier cleaning. Preferably, the hopper is configured so that it is as close to the ground as possible in order to ensure a low center of gravity to avoid tipping of the device. The hopper may be configured to be automatically refillable.

As depicted in FIG. 3, hopper 424 contains a volume of food (in this example about 500 mL), and is in communication with a protected conveyor channel 422. The conveyor conveys the volume of food 146 to the tray 148 of the presentation platform 150 while the tray is in the staging area (underneath 422). Hopper 424, conveyor channel 422, and angle guide 420 are attached to adapter 430 by fasteners. One of ordinary skill in the art will recognize that a variety of fasteners may be used including screws, rivets, and glue. Motor assembly 426 is attached to the hopper end of protected screw conveyor channel 422. A variety of different motors may be used including battery powered electric motors, DC powered electric motors, and the like. Batteries may be located in a suitable location in the device, but preferably on base 400. Adapter 430 is attached to base 400 by fasteners. Optional legs 410 may be attached to base 400 by fasteners. Presentation platform 150 is disposed between adapter 430 and base 400 by a rotatable assembly in this figure. The rotatable assembly can include an axle, ball bearings, a variety of lubricants, and the like. One of ordinary skill in the art will recognize various other methods of providing a rotating presentation platform between adapter 430 and base 400. FIG. 4 represents a cross-section of FIG. 3.

FIG. 5 represents presentation platform 150 having a bottom (FIG. 5A) and top (FIG. 5B). FIG. 5B depicts the food 146 in the food tray 148. FIG. 6 is a cross-sectional representation of presentation platform 150, and FIG. 7 provides a perspective view of the assembly without the conveyor, which is described infra.

Food Presentation

In order to accomplish the goal of presenting food to the animal for a finite period of time, a method of removing access to the food is required.

In one configuration, after the food has entered a staging area, and as provided in FIGS. 3 and 4 for example, it is added to a food tray 148. Food tray 148 is located toward the periphery of a presentation platform 150 that turns under power from a motor given a command from the controller to rotate the food tray 148, bringing it from a location in which its food was protected from the animal to a space on the unit designed to facilitate animal consumption of the food.

In one configuration, and as depicted in FIG. 7, the motor 814 is connected to the tray via a spring-loaded friction gear. As depicted in FIG. 8, this gear consists of a motor 814 in communication with a spring-loaded friction gear 902 which is subsequently in communication with the outer periphery of the presentation platform 150. The turning of the motor thereby causes the rotation of the presentation platform gently and in such a way as to eliminate the possibility of injuring an animal that has, for example, placed one of their paws on the presentation tray. The friction gear serves to limit the maximum amount of force that the presentation platform can apply by slipping once it encounters enough resistance, thereby eliminating the possibility that enough force could be applied to cause injury to an animal.

After food presentation, the controller causes motor 814 to enter inspection mode and uses a detector 520 (not shown, but see FIG. 12 for location) pointing down at the appropriately positioned food tray 148 to determine if food remains in the dish. The inspection can happen as the food tray 148 passes underneath the detector, or the tray can stop underneath the detector.

In one configuration, in order to ensure that food particles 146 are in the middle of the food tray 148, the controller can execute a "food centering" program that shifts the food tray back and forth. If food remains, the platform can enter "ready mode" with the last food particle.

In one configuration, the spring loading on the friction gear 910 can be adjusted to increase or decrease power transfer to the platform, depending on the safety requirements of the device.

In other configurations, the presentation platform may be locked in position via a locking mechanism. In certain configurations, this locking mechanism is controlled by a servo motor, and in other configurations it is controlled by a solenoid. In certain configurations there is a locking mechanism for each desired controllable position of the presentation platform (e.g., one for the reception mode, one for the ready mode, and one for the presentation mode). There can also be a single locking mechanism that can lock the presentation platform in an arbitrary location.

Conveyor

One configuration of the device uses a screw conveyor as depicted in FIG. 4 as conveyor 522 and also FIGS. 9A and 9B to deliver food (not shown) from the hopper 424 to the staging area. One example of such a conveyor is provided in U.S. Pat. No. 1,892,206 which is incorporated herein by reference. Such a conveyor can transport heterogeneous varieties of particles up slopes.

As depicted in FIGS. 9B and 10, the conveyor can consist of a screw 512 connected to a motor 510 that turns the screw 512 within a screw conveyor channel 422. The screw 512 is designed for low friction contact between the objects it is moving and the screw itself. The channel 422 serves to keep the items in contact with the screw 512 but not attached to it, allowing the screw's turning to cause particles in the channel 422 to move. If the screw is helical and "centerless" it is spring shaped and particles with a diameter less than the diameter of the screw can be thus conveyed. If the screw has a center then only particles less than the distance between the edge of the center of the screw 512 and the screw channel 422 can be conveyed.

The screw 512 can be understood to have one long spiral blade. Along the bottom of the channel the screw makes a close approach at a number of points. It is at these points that the particles are pushed by the blade. Looking at the screw from any lateral side the helical blade appears as a series of lines called "fans". The distance between each fan is the screw's "pitch". In the case of a centerless screw, the blade can be flattened and its shortest dimensional extent described as its "thickness", with its second-shortest dimensional extent described as its "width".

Still with respect to FIGS. 9B and 10, the screw motor 510 may be designed to rotate the conveyor either a fixed or a variable amount. The motor is in electronic communication with a controller (not shown) that can cause it to rotate either in only one direction (the delivery one) or in both.

The controller can signal to the motor 510 that it rotate a predetermined fixed amount, or that the motor 510 continue rotating incrementally until the controller instructs it to stop rotating. This latter approach allows the controller to cause the screw conveyor to continue conveying until food is detected in the food tray 148, minimizing the possibility that either no food will be delivered to the staging area, or that too much food will be.

Typically, when particles are being conveyed, either their dimensions are well-specified in advance (allowing for easy separation of them into singletons), or they are conveyed in particle groups of varying sizes. When both the particles vary considerably in size (e.g. by a factor of 10) and there is a need to controllably select single pieces of them, existing solutions include: (a) machine vision in combination with a controllable grabbing device, (b) vibration of the particles through a dimension-constrained trough, or (c) movement of particles (stacked one high vertically) over a perforated platform.

The key functions that such a device must perform are: (a) ensuring that free flow of the particles is not impeded, (b) that particles exit the conveyor one at a time (and can thus be dispensed on demand), (c) that the physical integrity of the particles is preserved, and (d) that the conveyor can handle particles that vary considerably in shape (e.g. some particles being more flat, others being more spherical) and size (when the smallest particle in a group of particles is size "X" the largest particle in the group is up to twenty-times that size, or "20X", e.g., 0.2 cm-4.0 cm). Additional desired functions include: (1) consuming relatively little space relative to the particles' dimensions, (2) being relatively quiet, (3) being durable, (4) being easy to clean, (5) permitting a low center of gravity, and (6) being inexpensive to manufacture. As noted above, existing approaches cannot accomplish (a) through (d), and not in combination with (1) through (6).

In one example, as depicted in FIG. 4 as conveyor 522 and FIGS. 9A and 9B, the conveyor consists of a helical screw conveyor 512 connected by shaft 1100 to a controllably powered motor 510 (FIG. 10). The screw conveyor is in communication with hopper 424 in such a way as to minimize or eliminate grinding or disintegration of food particles (not shown) to be conveyed, and in such a way as to eliminate the possibility of freezing or jamming of the screw conveyor 512 (provided particles are smaller than a particular size). Particles from the hopper enter the screw conveyor 512, which resides inside channel 422, perhaps a few at a time, at the hopper end. Particles travel through the screw conveyor until they reach the delivery end. Because screw conveyor 512 is tilted upward, it serves to prevent particles from stacking on top of each other. At the delivery end the conveyor dispenses particles one at a time. A detector 518, positioned at the delivery end, detects the delivery of a particle, and communicates this to the controller that is in communication with the motor.

FIG. 14 provides a method for delivering food via the conveyor. In this figure is described a method of extracting a piece of dry food from a volume containing many of them. The controller begins in a state of needing to dispense a food reward. If the controller detects that there is already some food in the food tray via information obtained from detector 520, then the controller is programmed to infer that the requirement has already been satisfied and doesn't operate (food has already been dispensed). If, however, there is no food in the food tray, then the controller rotates the conveyor a small increment while receiving input from the detector 518 and analyzing it to determine whether some food drops from the conveyor to the tray. If the drop detector 518 is tripped, then it's assumed that the food has been dispensed. This can be confirmed via input to the controller from detector 520.

One way to bring food from the hopper 424 to the staging area is to have one end of a screw conveyor 512 exposed and located such that gravity causes food from the hopper to be in physical contact with blades of the screw conveyor. In this case, the remainder of the screw conveyor may be enclosed (e.g., in channel 422) in order to minimize grinding of food particles and the torque load. The food enters the screw conveyor 512 at the hopper end of the conveyor and transports it through the conveyor channel to the staging area (in one configuration, the tray-sized volume directly below 518). Because the screw conveyor can transport particles in opposition to gravity, it can allow a lower center of gravity for the hopper by taking food from lowest possible point in the device, minimizing possibility that the device could be tipped over.

Advantages of using a screw conveyor include: ability to handle a variety of food sizes; intrinsic resistance to jamming; simplicity—screw conveyors can convey effectively with only one motor and one moving part. The screw conveyor can be configured such that, at its hopper end, its circumference is exposed to the hopper anywhere from 5 degrees to 270 degrees. The smaller the angle of exposure to the hopper end of the screw degrees the smaller chance of grinding food particles. The more degrees it is exposed (up to the smaller the chance that food will jam or bind, preventing further food from entering the conveyor at the hopper end. FIGS. 11A and 11B provide optional tilt adjustment for the conveyor (FIG. 11A being level, and FIG. 11B being tilted at a desired angle). FIGS. 12A and 12B provide cross-sectional depictions of the same.

Further advantages are provided in Table 1:

TABLE 1

| The screw conveyor can be designed in various ways to: | |
| --- | --- |
| A. | Maximize the range of food types that can be conveyed: it may do this by being an open, "center-less" spiral that allows for food particles with a diameter longer than the radius of the screw conveyor; |
| B. | Minimize food particle grinding it may do this by having a soft plastic coating on the screw conveyor, or by making the conveyor itself out of a softer plastic. |
| C. | Minimize the need for cleaning: the conveyor can be designed with tight tolerances that allow it to "self clean"ensuring all food particles (even powder-sized) leave the hopper and conveyor and are delivered to the staging area. |
| D. | Maximize ease of cleaning: the conveyor can be designed to be easily taken out. It can be designed out of a material that allows it to be "dishwasher safe". It can have on it a coating that prevents the accumulation of oil-based dirt. |
| E. | Maximize ease of replacement: Either just the screw, or just the motor, or the screw and the motor it is connected to can be configured to be removable from the unit and replaced. It may be advantageous to replace only the screw portion in order to accommodate different kinds and sizes of food. It may be advantageous to replace the screw in order to address problems with screw failure. It can be connected to the motor in such a way that a releasable clamp is used to affix the screw to the motor. When the clamp is released, the component of the screw conveyor can be taken outf or cleaning or replacement. |
| F. | Maximize robustness: By making the screw out of metal the screw can have maximal strength and flexibility, preventing failure of the screw. |
| G. | Minimize quantity of food dispensed: Appropriate choice of conveyor channel angle causes food not in direct contact with the conveyor channel to fall backward toward the hopper end of the screw, minimizing the frequency of events wherein food is delivered to the staging area in a cluster rather than as an individual particle. |
| H. | Minimize conveying failure: By increasing the width of the blade of a centerless screw, the probability that food will fall inadvertently down the conveyor channel can be minimized. |
| I. | Minimize the probability that food at or near its delivery end will enter the staging area in an uncontrolled way: By adjusting the angle of the delivery end "cliff" relative to the angle of the conveyor blade it is possible to preference the dropping of certain particles from the conveyor shaft. By selectively changing the blade so that it is no longer optimized for low friction, e.g. by corrugating it, it is possible to perturb treat groups, and minimize the probability that the entire group will fall simultaneously. By adding a miniature shovel-like addition to the blade (e.g. a piece protruding parallel to the extent of the channel and nearly orthogonal to the blade) near the delivery end, and configuring the channel so that it is first opened laterally, the screw conveyor can transition from moving pieces along the extent of the channel and instead up what had previously been the channel's sidewall. This will cause food clumps that have distributed themselves horizontally along the screw to be conveyed in a piecemeal fashion from the conveyor. |

Therefore, in yet another embodiment of the present invention, a conveyor is provided for controllably conveying particles from a hopper to a staging area a single particle at a time, wherein the particles are non-uniform in size and shape and restricted in diameter to between a range in size X to size 20X. In various aspects, the particles are clumps of food. In yet another aspect, the food particles range in size from 0.2 cm to 4.0 cm.

Conveyor Control

As depicted in FIGS. 12A and 12B, in the case of a conveyor 522 that uses a "continuous feed" method (such as a screw conveyor) to bring food from the hopper to the staging area, a capability of detecting the delivery of one or more treats to the staging area can allow for programmatic control, thereby permitting stopping of the continuous feed when the dispensing of food has been detected.

Still referring to FIGS. 12A and 12B, a detector for the conveyor control is located so that it detects drop events from the delivery end of the conveyor 518, or it can be located so that it detects the presence of food particles in the staging area tray 520. This detector can be in electronic communication with the controller, and thus be used, for example, to create a closed loop system that allows a variable quantity of treats to be delivered to the staging area.

If the detector is positioned to detect food particle delivery events, and not only the presence of food particles in the tray, the device can be configured to deliver 2, 3, 4, 5, 6, 7, 8, 9, 10 or more treats to the staging area by having the controller count food particle delivery detection events, and running the conveyor until the number of detection events has been observed.

Staging Area

The staging area serves to hold food that is ready for presentation to the animal upon command from the controller. One configuration of the device has the controller only delivering food to the staging area when the device is in reception mode. Referring to FIGS. 12A and 12B, the staging area is depicted immediately below detectors 518 and 520. In another example, the device could be configured to hold food particles in the staging area and then have gravity bring the food into the tray when the presentation platform 150 enters reception mode.

Food Tray

In one configuration, the food tray 148 (as provided in various Figures) is removable, allowing for replacement with others and easier cleaning. In one configuration, the food tray 148 uses magnets to stay connected to the presentation platform 150. In certain configurations, the food tray may be constructed of stainless steel, in certain other configurations, the food tray may be constructed of animal-safe plastic.

Controller

In one configuration, the controller is an operator-programmable micro-computer that can connect to other computers wirelessly. The controller can be programmed either locally or remotely. In one configuration, it can be controlled in real time by an operator. It can be located under housing 102.

Sensors

In one configuration, multiple microphones are provided in order to determine the location of sounds in the environment of the system. In one example, the system uses the difference in sound arrival times to determine the source direction of the sound. With two microphones, the location of the sound can be identified two dimensions (along a plane projecting from the microphone array). With three microphones arranged in a triangle, a three dimensional vector can be inferred. Added microphones increase the accuracy of the sound localization. Another use of multiple microphones is the application of source separation: if multiple sound sources are mixed within a room, Independent Components Analysis can be used to de-mix and isolate individual sound sources for further processing. This may help with animal identification and sound-based methods of determining the animal's condition.

In another configuration, one or more microphones are used to sense contextual information. A microphone can be used to identify the existence, content, and valence of human speech in the vicinity of the microphone, information that can be used to sense whether, for example, an operator is frustrated or happy with the behavior of the operator's pet. The microphones can also be used to detect events that might be distracting, alarming, or distressing to the animal. This can be used to inform the system of potential resulting changes to the animal's condition, which allows the system to adjust its programming appropriately. The system can also correlate sound events with changes in the animal's behavior, information that can be used to inform the programming of the system on future events and to inform modifications to the programming of how the system responds to other animals.

In another configuration, sound information from the environment can be recorded. Sound information that reliably predicts the elicitation of particular animal behaviors (e.g. excessive dog barking) can be presented to the operator so that the operator is informed of the relationship between environment sounds and animal behavior.

In another configuration, the microphones are used to register the volume of the overall ambient noise level. In another configuration, the microphones are used to identify human speakers.

In another configuration, one or more microphones are used by the operator to record specific replies to particular animals (e.g. "good dog!"). In another configuration, the microphone can be used to record sounds that are already intrinsically rewarding to the animal (e.g. the sound of an opening can). In another configuration, one or more microphones are used to sense dog barking, animal whining, animal purring, or animal urination.

In another configuration, an ultrasonic sensor is used to calculate the distance of the animal from a point in the room (e.g., the animal's distance from the device). This distance information can be transformed into a feedback signal to the animal that serves to compel it to approach a particular distance from the sensors. The ultrasonic sensor can also be used in conjunction with touch sensors on the device to accelerate the animal's learning of an association between the touch sensors and earning positive reinforcement by reinforcing early events wherein the animal only approaches the button.

In another configuration, visual sensors are used to determine the animal's posture or track the location of one of the animal's body parts. This allows the system to use techniques of successive approximation to communicate to the animal which posture or movements the animal should perform. For example, the system could recognize the posture for "sitting" and provide a real-time feedback signal that communicated to the animal how close the animal was to sitting down. By tracking particular animal body parts with a visual sensor, the system can provide real-time feedback that communicates to the animal where in space it should move this body part. For example, it could provide a feedback signal tied to the location of the animal's nose, and use real-time feedback to communicate that the animal should touch its nose to a particular part of the floor. One approach to implementing such a sensor would be use a MICROSOFT® KINECT® (or similarly working variant thereof), which provides visual depth information more amenable to computer vision processing. Another approach would be to use a LIDAR-based visual sensor. Still another approach would be to use a stereoscopy-based depth camera approach (two cameras that use parallax information to infer visual depth). Still another approach is to use a single camera with advanced software that is able to extract depth information from a 2D video stream.

In one configuration, touch sensors are used to detect contact the animal makes with the animal interaction device or another component of the system. Such sensors may be designed to encourage animal interaction, perhaps via embedded visual stimuli. These touch sensors are designed to be "animal-touch friendly", and accommodate touches from paws, noses, and other animal body parts. These sensors are designed to resist, deter, or render impossible biting, scratching, or other animal-caused mangling. They are also designed to handle repeated and prolonged use. These touch sensors may be illuminated by LEDs or other forms of animal-visible illumination. These touch sensors could be user removable and replaceable in order that the device they are embedded within can be easily repaired if broken. Such touch sensors may be differently sized to accommodate differently—sized animals. Such touch sensors would be designed to be extremely sensitive to the light presses of a kitten, while simultaneously durable to the heavy presses of a German Shepherd.

The touch sensors could be variously implemented using a lever, a "brush-by" sensor, a haptic sensor, a capacitative touch sensor, or a pressure sensor. If the touch sensor is pressure-sensor based it will be able to provide more information to regarding the engagement of the animal.

In one configuration, an accelerometer sensor on the animal could be used to evaluate the animal's activity level and animal behaviors. Animal behaviors such as "sit" and "stay" could be inferred from data on from the accelerometer. Data from the sensor could be stored locally or on a remote computer, and combined with data from other animals. The animal's activity level could also be determined from the sensor, providing useful information to the system that could be used to help classify animals and improve animal interaction algorithms. Such a sensor could be implemented using a WiFi-connected animal activity monitor, either in direct communication with an animal interaction device, or in communication with a remote computer capable of communicating with an animal interaction device.

In one configuration, a thermocouple could be used to infer the ambient temperature of components of the system. For example, a thermocouple temperature sensor located on the unit could be provide information allowing the unit to alter its behavior depending on the device's ambient temperature.

In one configuration, a "lickometer" sensor could be used to measure the propensity of an animal to lick a component within the system. Animal licking behavior data can be used to infer aspects of the animal's condition.

In another configuration, an infrared beam-break sensor is used to detect the animal's presence or absence near the animal interaction device or in relation to another component of the system. This sensor could be used to detect the approach of an animal part to a particular part of the system, providing valuable information to the controller and remote computer regarding the animal's condition.

In one configuration, a food weight sensor could be used to detect the quantity of food being eaten (or not eaten) by the animal. Such a sensor would provide valuable food information to the local controller or remote computer, for instance regarding the popularity of different kinds of food or treats.

In one configuration, a passive infrared sensor is used to detect whether an animal has approached the device, or is in the same room as the device or a component of the system. With a passive infrared sensor, the system can also infer the animal's body heat, providing additional valuable information regarding the animal's condition.

Indicators

In one configuration, the device can provide feedback to the animal. Three kinds of feedback can be provided: positive feedback (i.e. positive reinforcement: for example a reward, such as a bit of food or treat), aversive feedback (i.e. negative reinforcement: for example, in the form of an annoying sound), or informational feedback (for example "owner will be returning soon"). Different kinds of informational feedback include "food will be served soon", "this is a pattern you should remember", or other kinds of information the operator may want to communicate.

There are various ways of providing positive, negative, and informational feedback. One approach is through sound from speakers. A speaker could be programmed to play a "grating" sound, or a "loud" sound, or an audio (and potentially video) recording of the owner chastising the animal. Ultrasonic sounds can be an effective method of providing negative feedback, and has been deployed as a simple form of bark mitigation (for example, when dog barks are detected the device plays a high volume ultrasonic sound that startles the dog and temporarily eliminates the barking). Positive feedback can be provided via recordings of the owner's own voice, food rewards, arousing sounds (such as that of a crackling a disposable PETE plastic bottle), a favorite animal "squeaky toy", the sound of a puppy crying for its mother, the sound of a small animal in distress. Positive (but less arousing) sounds include the sound of a rustling treat bag/bottle, the sound of a can opener.

In another configuration, lights can be used as indicators to the animal. These lights can each be associated with a particular button or with the overall context of the device. The lights can be have their color and brightness programmatically controlled, and flashing the lights could also serve as aversive feedback to the animal. The coloring of the lights themselves would be chosen to as to be meaningful and visible to the animal based on the color gamut available to the animal.

In another configuration, a favorite toy can be made accessible to the animal as a positive reinforcement, or protected from the animal as negative reinforcement. The toy could be made visible to the animal, or the toy itself could be fixed behind a hatch within the device: the toy would be made accessible by lifting the hatch, and protected by having the hatch descend.

In another configuration, a video display can be used to provide any form of feedback. In the case of informational feedback, a video display could be used to demonstrate to an animal how to perform a particular task. For positive feedback, the video display could present an image of the owner's face. For negative feedback, the video display could flash quickly and brightly, or display images that the animal does not like (e.g., the owner's body with its back to the animal).

In another configuration, the provision or removal of an odor could be used to provide positive, negative, of informational feedback to an animal. The provision of a pleasant odor could serve as positive feedback. The provision of a negative odor (or the removal of a pleasant one) could serve as negative feedback. The odor of the owner could serve as a kind of either positive of negative feedback. The provision of the odor of an object to be searched for or retrieved would serve as informational feedback. In another configuration, catnip could be made accessible or protected to provide positive or negative feedback to an animal.

In another configuration, the animal interaction device, or a component of the system described here, could turn itself "on" or "off" as a form of positive or negative reinforcement, thereby using engagement with the device itself as a form of reward for the animal.

In another configuration, the animal's capacity to taste can be used as positive or negative reinforcement, with a "bad taste" serving as a negative reinforcement.

System

As depicted in FIG. 13, and in another embodiment of the present invention, a system 1300 is provided for interacting with at least one animal. The system comprises various components which operate together to automatically interact with an animal. FIG. 13 provides an example of such a system.

Therefore, and in an embodiment of the present invention, a system is provided for automatically interacting with an animal including at least one animal interaction device each of which comprises an initial interaction algorithm to automatically interact with the animal, the initial interaction algorithm further comprising device instructions selected from the group consisting of (a) presenting stimuli, and (b) continuously or intermittently recording variables selected from the group consisting of the animal condition, the device state, and the time of such recording, and (c) controlling the timing and duration of the presentation of reinforcement selected from the group consisting of positive and negative reinforcement, wherein the intermittent recordings are transmitted to at least one remote computer, and further wherein the at least one remote computer is programmed to modify the initial interaction algorithm informed by the intermittent recordings, and transmit the modified interaction algorithm to the at least one device to replace the initial interaction algorithm.

In various aspects, the animal interaction device provided in the system is the device first described above. In other aspects, the animal interaction includes, but is not limited to, training, modifying the behavior, and modifying the condition of the animal. In yet other aspects, the positive or negative reinforcement is removed from the animal.

In another aspect, data from continuous or intermittent recordings are segregated and inform the modification of the initial or modified interaction algorithm of the at least one animal interaction device. In yet another aspect, the initial interaction algorithm is downloaded upon starting the device. In another aspect, the interaction algorithm is housed on the at least one remote computer, and instructs the at least one animal interaction device to perform the instructions.

Still referring to FIG. 13, the system can include one 1310 or a number of devices 1350 as described above, communication 1330 of the devices with one or more remote computers 1360 over a network, a set of data 1362 generated by the devices, the ability to analyze data from one or a number of other devices 1364, the ability for the software programming 1322 of the devices to be updated 1366, and the ability to use the analysis of data from other devices to update programming of a device.

Therefore, a system 1300 is provided for automatically interacting with an animal, the system comprising at least one animal interaction device 1310 comprising a pre-programmed interaction algorithm 1322 to automatically interact with the animal, the pre-programmed interaction algorithm further comprising device instructions selected from the group consisting of: (a) presenting stimuli 1313; and (b) intermittently recording variables selected from the group consisting of the animal condition 1315, the device state, and the time of such recording; and (c) controlling the timing and duration of the presentation of reinforcement 1317 selected from the group consisting of positive and negative reinforcement; wherein the intermittent recordings are transmitted to a network of servers 1324; and further wherein the network of servers are programmed to receive the intermittent recordings from the at least one device, and programmed to modify the pre-programmed interaction algorithm 1366 informed by the intermittent recordings, and transmit the modified interaction algorithm 1326 to the at least one device to replace the pre-programmed interaction algorithm.

Optionally, the system can include the ability to update the timing of food removal, and use data providers to provide data integration algorithms such as a visual depth sensor, e.g. a MICROSOFT® KINECT® feature, LIDAR, and stereoscopic-based 3D can be integrated in the system.

More particularly, the components of the system include: a device as described above 1310, software logic 1322, 1364, 1366, interaction data and knowledge data 1362, system operators, an operator interface 1380, communications 1330, and optionally a social network.

A component of the system is the device described above 1310. The device can also interoperate with external hardware including other toys which may have wireless communication capability, external microphones, external cameras, external computers, other external sensors, and the like.

Another component of the system is software logic 1322, 1364, 1366. Such logic can be preprogrammed on the device or generated dynamically using various inputs, for example via the Internet. Preprogrammed software on the device 1322 can involve a combination of controller (i.e. local) and remote computer (e.g. server-side) programming, with controller-based programs controlling local interactions. Such preprogrammed software logic may be programmable by operators 1384 and/or entirely programmed and/or executed by a remote computer.

Software logic can also include device updating logic 1366. Examples of such logic include instructions on the device to query another computer for the existence of a possible update to the device's logic, and, if another update is available, instructions to perform the transmission of updated logic from the other computer to the device 1326, and the replacement of the currently operating device logic with the updated logic, so that the device's behavior is appropriately changed. Another example of device updating logic would occur when another computer examined the recorded variables from the device and, potentially informed by information from other devices, decided that it would be beneficial if an update to the device was performed, subsequently notified the device that an update was suggested, and then the device pulled the updated logic from the other computer and changed its behavior according to this newly updated logic. Software logic may also involve analysis such as the application of machine learning algorithms and techniques. For example, machine learning can be used to perform inference, such as determining the timing of certain events. Machine learning techniques can also be used to perform classification on animals, determining their group or subgroup, and when applied to data from many devices, it can be used to identify clusters of animals that are similar in a particular respect. For example, machine learning techniques can use clustering techniques to place a particular animal into a group or sub-group based on the data acquired from this and other animals. Machine learning can also identify parameters, e.g. via statistical regression, which can be based upon knowledge of the animal's group/sub-group.

Software logic can also include artificial intelligence programming and algorithms which can be used to make decisions and perform actions. These decisions and actions can impact the updating of the software on the device by adjusting decisions to update the device, as well as decisions about the configuration of the updated software logic. The decisions can also affect the type, nature, timing, and context of stimuli and reinforcement presented to the animal, even in real time. Artificial intelligence software logic can include knowledge of animal's state and can be designed to make decisions about a series of iteratively updated animal interactions so that the animal's condition reaches a particular goal state. For example, the operator of the device could set as a goal state that the animal should be as active as possible, and the artificial intelligence software logic will then choose stimuli, timings, and other device behaviors with the aim of achieving this goal.

In another aspect, software logic can include collaborative filtering by operators. Operators can rate and rank different variations of the software programming 1386, information which can be used to modify the programming of the device. In this way, operators can contribute to the refinement of the software programming by providing feedback related to the impact of different programming.

The system also includes interaction data 1362. The system can provide and utilize the full history of animal interaction with the device, including a log of details of every interaction, such as timestamp, buttons pressed, sounds played, lights illuminated (color and brightness), and all information available from all sensors.

The interaction data may also involve communication between devices. Two animals, each at one device, can each make sounds that would be sensed by their local device and transmitted to the device of the other animal. In a particular unit, interaction data may be communicated to other units.

Data from the units of other animals can be directly used to inform the programming of a particular one. The system allows for predicting how an animal will respond to stimuli from a particular unit, even though the circumstances with this particular animal are new to this animal. It does so by searching for similar behavior patterns between animals. To the extent that the local history of a particular unit or animal matches the history of another unit or animal (or of a group of units or animals in aggregate), the local unit can make predictions for how the animal will respond, and adjust its programming such that its prediction of that the animal will achieve some goal state is intermittently or continuously maximized, while its calculated effort to reach this goal state is minimized.

Knowledge is also part of the system. For example, scientific knowledge may be provided in the system, such as cognitive models (e.g., emotional state and learning state), reward schedules, breed differences, sex differences, and species differences. Such knowledge can be used in conjunction with the software programming to enhance the device interaction with the animal.

The system interacts with a variety of operators 1380. The operator can input information in the system to modify the way the device interacts with an animal or animals 1384, 1386. For example, the operator can input goals for animal behavior 1384 such as activity level, diet, and response to instructions (e.g., "come here" or "press the left button"). The operator can also input information with respect to personal information 1386 (e.g. from Facebook profile), number of pets owned, number of devices owned, and provide audio cues (record their voice to be played back as a stimulus from a speaker), and the like.

An animal (the one interacting with the device and system) can have information input in the system by an operator such as its species, breed, age, sex, neutered/spayed, activity level, times walked/week, rural/suburban/urban, operator-uploaded pictures, etc. Such information can be used to enhance the device interaction with the animal.

Interfaces are also part of the system. An interface on an external device (such as a phone, tablet, browser/computer) can be used to interact with the device 1380. On the device, buttons, at least one microphone, at least one light, etc. can be used to input information on the device.

In another aspect of the system, communication can be implemented between the system and with remote computers 1330, for example, via WiFi and via fiber optics. Communication can be implemented between the operator and the system via servers (optionally), via WiFi ("direct" communication), and via "push" notifications of pet progress. Communication can be implemented between the system and with the animal directly via the device.

In another aspect of the system, an online social network may optionally be used as part of the system. For example, information used in the system can include pet profile information, "leaderboards" (such as the ranking of animals interacting with the device and system), various media (such as videos of pets, videos of pets interacting with device, and images of pets), software programming reviews (providing information regarding collaborative filtering and programming quality, for example), and even pets "friending" each other via a social network.

The system described herein can also be viewed and operated according to the flowcharts depicted in FIGS. 14 through 19.

In yet another aspect, a method of integration of the device and the system is provided in which the device is wholly controlled by a remote computer (e.g., a "server" or "the cloud"), thereby necessitating no, or minimal, software on the device. In this configuration, the device acts as a "dumb terminal", in which a remote computer has more control over the device's behavior. In this case, some or all of the information from the device's sensors and detectors is transmitted, perhaps within seconds or milliseconds, to the remote computer. The remote computer might then perform operations that integrated the information communicated by the device into computer software and analysis performed on this remote computer. Subsequently, the remote computer could communicate back to the device information as to what the device should effectuate or output, information such as when to reward the animal with food, or information such as sound data for the presentation of stimuli to the animal via one or more indicators.

As a "dumb terminal", no, or only few, instructions on how the device should interact with an animal need to found on the device at any point in time. The device can be installed and begin operating and rely entirely on information provided in "real time", or approximately "real time", in order to respond effectively. The controller on the device serves primarily to relay information from the device's sensors to the remote computer, and to execute instructions from the remote computer on the device.

Methods

In yet another embodiment, a method of animal interaction is provided, including the acts of providing a device first described above to an animal, and optionally activating one or more indicators, and sensing the animal's condition via one or more sensors, and based upon the animal's condition making previously protected food accessible, and subsequently making the food protected again based upon the animal's later condition. In various aspects, the later condition of the animal is the same as the prior condition of the animal. Those of skill in the art will understand other methods of using the device and system of the present invention.

Kit

A kit is provided which includes the device described above, and instructions for operating the device. Both the device and instructions are packaged in a box suitable for storage, for example on a store shelf or for delivery through the postal service. The kit can also include labeling, power cables, batteries, DVD and/or other information-conveying media, disposable products associated with the device, and other packaging materials.

Device Shape

As the device will be enticing to animals as a source of food, animals will no doubt attempt to access the protected food by breaching or otherwise accessing the protected volume. The device can be designed to account for these attempted intrusions in a number of ways. In certain configuration, the device is configured to have a low center of gravity to make it difficult to tip or knock over. In one configuration this can be achieved by designing the hopper to have the majority of its volume as low to the ground as possible; in one configuration this is achieved by having the screw conveyor hopper end lower than the screw conveyor dispense end, so that the food can be accessed at the lowest possible point of the device, and therefore the food itself can act as a ballast.

Accordingly, in yet another embodiment, the device first described above is provided having a base diameter at least twice the height of the device.

In another configuration, the low center of gravity is achieved by composing the bottom of the protected volume of a heavy material, such as a solid metal like steel or cast iron, or a dense plastic. In certain configurations, the low center of gravity can be achieved by including some form of ballast at a low point inside the device such as metal, stone, weights, a reservoir for water, sand, gravel, or some other heavy, free-flowing material.

In addition to a low center of gravity, certain configurations can reduce the likelihood that the device is tipped or knocked over by providing a way to attach the device to the wall or to the floor, or to some other larger, sturdier object. In certain configurations, the device may be bolted, screwed, hammered, glued, epoxied, attached by straps, attached by wires, attached with cords, attached with brackets, or attached by some other means to the wall or to the floor to some other sturdy object in the service of avoiding the tipping or knocking over of the device.

In certain configurations, a breach of the protected volume containing the food can be avoided by ensuring that the outside of the device contains as few as possible accessible joints, seams, or edges that may be manipulated in order to either move the device physically or to gain purchase to flip or overturn the device. In certain configurations the outside housing can be made to be dome-like, so that the exposed surface is as smooth as possible and so that there are no places to gain traction with a paw, or claw, or nail, or hand, or foot.

Since the way food is made non-protected is by sliding through an opening in the protected volume, the junction between the presentation platform and the outer housing is especially important. In certain configurations, this junction is made with very tight tolerances, so that there is no part of an animal that may slide between the presentation platform and the outer housing. In certain configurations, this junction is supplemented with a brush or rubber gasket or squeegee that ensures a tight fit between the presentation platform and the outer housing. In certain configurations, the system that drives the presentation platform is driven by a motor system that has a clutch that disengages the drive system from the presentation platform in the event that the platform requires torque above some functional threshold, indicating that something is stuck, most probably at the presentation platform-outer housing junction. This may be a piece of food in an unlikely place, or it may be some other foreign object, or it may be a part of an animal, such as a paw from an animal attempting to manually move the platform to obtain a protected portion of food. This clutch will therefore serve as a safety mechanism for the animal and also as a safety mechanism for the device.

EXAMPLES

Aspects of the present teachings may be further understood in light of the following examples, which should not be construed as limiting the scope of the present teachings in any way.

Example 1—Food Dispensing and Removal

Food is held in a protected hopper which is protected in a housing, and can only be accessed by an operator. At the bottom of this hopper is a screw conveyor that can transport pieces of the food from the hopper, through a protected screw conveyor channel, to a protected staging area. The hopper end of the screw conveyor is exposed to the food, and the hopper is designed such that all food within it makes contact with the conveyor and can thus be conveyed to the staging area. The conveyor conveys by turning a screw within the channel that carries the food to the staging area. The food pieces are allowed to drop out of the conveyor into the staging area. The food's dropping is detected by a detector. A controller that is in communication with the detector can thus count the number of pieces of food dropped and use this to control the rotation of the screw conveyor in the channel, thereby allowing it to control the quantity of food arriving in the staging area. The staging area consists of a protected location from which food can be taken away via a tray on a rotating platform. The platform is in communication with a motor that rotates the tray and brings it into the staging area, leading gravity to cause any food within food drop area to enter the tray. Subsequent rotations of the platform can subsequently permit the food to move away from the staging area and then potentially be made accessible to the animal. Regardless of whether the animal eats the food, the tray can be moved away from the presentation area by rotation of the platform to again make the food protected. The conveyor aspect within this example is illustrated, in part, in FIG. 14.

Every instance of food dispensing and removal can be recorded by the device and reported to another computer via a computer network. This computer records each report, including when the food was dispensed, how much was dispensed, and whether the food dispensed was consumed by the animal. Using any network-connected interface (e.g. a tablet computer), an operator can inspect a visualization, or the raw data, of the recorded history.

Example 2—Animal Controls Food Access Directly

In one configuration, illustrated in FIG. 15, the device is programmed to dispense a portion of food from the hopper upon the animal's request, this request being sensed by the device as a particular change in the animal's condition. After the device has been loaded with an appropriate volume of food and the appropriate program of the device has been executed, the device can sense a part of the animal's condition and use this sensing of the animal's condition to dispense food. The device may need to provide some indication to the animal that food is ready to be dispensed from the device, for example, by providing a visual cue, a sound cue, or combination of these and potentially other cues. Over the course of a period of time, the device may repeatedly dispense to the animal a portion of food, potentially in response to repeated sensing of a property of the animal's condition. For example, the controller may use a signal that the animal has made physical contact with a touch sensor to sense the change in the animal's condition and dispense food.

By both dispensing and removing food, the device can more quickly train the animal to actively request food from the device. By removing the food, the device can more clearly inform the animal that the dispensing of food was in response to the animal's request, rather than to another property of the animal's condition. Removal of the food furthermore prevents food from accumulating when the animal does not consume it: such accumulation reducing the effectiveness of the reward information provided by the device to the animal via food by rendering this information less consistent.

As part of a system, the device may be in communication with a remote computer over a computer network, in which case the remote computer can record the history of dispensing results and whether different cues were effective in indicating to the animal that food was ready to be dispensed. The other computer can use the results from this device, and potentially many others, to communicate information to the device concerning which different alternative cues may be more effective at indicating to the animal that food may be ready to be dispensed. For instance, perhaps the device had been using a cue of type A, but found that it was only effective at a rate of 30% (i.e., only three in every ten times when it cued the animal that the device was ready to receive input from the animal did the animal provide the input); afterward, the device changed itself to use cues of type B, and found effectiveness of 60%; other computer that is in communication with the device can then propose a cue of type C based on recognizing the A:30%, B:60% pattern from observations collected from other devices, and predicting that type C is more likely to yield better results than type D or E.

Example 3—Cued Device Interaction

In one configuration, illustrated in FIG. 16, the device is programmed to interact with an animal from time to time by presenting a set of sound and visual stimuli that indicate an action (for example pressing the rightmost button or pressing the leftmost button) for the animal to take in order to be dispensed food. That is, during each interaction, the animal must make one of two actions, the correct action indicated by the stimuli, in order to receive a food reward. The controller is programmed to wait a variable interval (for example some interval between 30 seconds and 600 seconds) between interactions.

When an interaction time is reached, the controller randomly selects one of the two actions for the animal to perform, and presents stimuli that are associated with the desired action from the animal. For example, if a left button press is the desired outcome on the current interaction, the left button will be illuminated and a low tone (1 kHz, or some other sound stimulus associated with the left button) will play from the speaker, whereas if the right button press is the desired outcome, the right button will be illuminated and a higher-pitched tone (6 kHz, or some other right-associated stimulus) will be played from the speaker. The stimuli will be present for some duration, and the animal will have this duration (and potentially sometime after the stimuli have been turned off) to make its response by either pressing the left or right button.

The controller senses the response made by the animal and determines the appropriate response. If the animal has made the correct action (for example, pressing the left button in response to the left stimuli), the controller will reward the animal by dispensing some food to the animal for a brief period of time (for example 2-10 seconds), after which time the food will be removed. By removing the food reward, the animal more strongly associates the reward period with their performance, since the animal can associate both the reward's being made available as well as its being removed. In addition to providing the food reward, a secondary non-food reward stimulus may or may not accompany the food reward. For example, a sound that indicates correct behavior may be played from the speaker.

If the animal makes an incorrect action (for example, pressing the left button in response to a left stimulus), the food remains protected, and the animal must wait until the next interaction to attempt to receive a food reward. In addition, a "correction sound" (for example, an aversive tone, or some other sound) is played from the speaker to indicate to the animal that it performed an incorrect action.

Integrated into a larger system, the device reports all of its actions and sensor readings to a remote computer. The remote computer maintains a history of these interactions, and in combination with histories of interactions of other computers and devices, sends information to the device controller regarding which frequency to use, the duration of food reward presentation, the kind of correction sound to use, and the timing of cue presentation to the animal.

Example 4—Slow Feeding

In one configuration, illustrated by FIG. 17, the device is programmed to feed the animal slowly, for example to ensure that the animal does not eat its meal too quickly and thereby risk digestive problems. When the operator has the goal of feeding the animal slowly, the operator puts into the hopper a quantity of food to be eaten by the animal. Then the operator executes the device program. The device may begin in reception mode, at which point the conveyor conveys one or more pieces of food into the food tray, and may optionally verify afterward that a piece of food has arrived in the tray. After a between-feed time interval (specified below), the device triggers the rotation of the presentation platform and putting the device into presentation mode. A portion of the food is thereby made accessible, in this case because the presentation platform is placed in presentation mode for a fixed, variable, or a random period of time, of between 1 second and 120 minutes. Afterward, the device may enter inspection mode and determine whether or how much of the food was consumed during the time when the device had most recently been in presentation mode. In doing so, the device likely removes the food, and this serves to provide information to the operator and the device about the animal's interest in food and its eating schedule. Food removal and inspection ensures that food does not accumulate in the food tray, and that the animal only ever eats a small portion of food at a time. The between-feed time interval may be fixed, variable, or random, and is chosen using an algorithm that may have as a goal ensuring that the animal is fully fed within a given time period.

Integrated into a system, this device is connected to other computers via a computer network. In one instance, the device is connected via a two-way network connection to a remote computer acting as a server. This remote computer could be connected to by any third computer with a network connection (that has the appropriate authorization). The "slow feeding/automatic dispensing" device configuration above would be selected by a user from a list of others through this third computer via a network connection. Through this third computer, and via the second computer, an operator of the device can select different specifications for the "slow feeding" device configuration, such as the duration of time that the food is presented.

Example 5—Stay Close By

In one configuration, illustrated by FIG. 17, that extends the configuration "slow feeding" above, the device is programmed with a shorter the time period during which food dispensed is accessible (i.e., varying the time between dispensing and removal; short FPD in FIG. 19). In this way, the device can reward the animal for being closer to the device. For instance, if food is only accessible for three (3) seconds at a time, then in order to have a chance to consume the food dispensed, the animal will need to be sufficiently close to the device. In this way, the device can train the animal to "stay close by".

Example 6—Come Here

In one configuration, illustrated by FIG. 17, the device is programmed to summon to the device the animal from another location. By providing stimuli that can be perceived by the animal when it is not in the immediate vicinity of the device, and then dispensing and making accessible food for decreasing periods of time after this stimuli is presented, the animal learns to go to the device more and more quickly, since arriving at the device too slowly after the presentation of the stimuli would result in not receiving the food reward.

In the example above, the stimuli presented could be customized so as to be the sound of a person's speech, for example saying "come here". By using a variation of the person's speech, and having this variation be sufficiently similar to the speech of a person living with the animal, the animal can learn to "come here" from the device and transfer this learning to the person.

Example 7—Triggered Come Here and Stay Close By

In one configuration, illustrated by FIG. 17, by combining the principles from the examples "stay close by" and "come here" with an external trigger, the animal can be compelled to go to and stay by the device on demand. For example, an operator with the goal of avoiding having the animal run out the door when it opens—the operator can execute the "come and stay close by" program on the device and thereby motivate the animal to stay within a particular space. In another example, the device can be triggered to execute the "come and stay close by" program whenever a door is opened or a doorbell rung. It should be clear that both the "come here" part and the "stay close by" part of this configuration require food removal in order to work effectively.

Example 8—Animal Moves

In one configuration, illustrated by FIG. 18, the device transitions the animal from a simpler interaction to a more sophisticated one. One of the settings made at interaction initialization is the choosing of an animal cue light; when selected, this light's luminance is set, its color chosen, and its blink rate configured. The system may optionally choose to dynamically change those settings of the cue light depending on its programming. Another setting made at initialization is a determination of what the food presentation duration will be: the time during which the animal will be able to access a portion of the food in the device. As with the cue light, the food presentation duration may also be a dynamic program of multiple presentations of varying durations, each of which is controlled by the device controller. Yet another setting determined at time of device interaction initialization is the total duration of the interaction: this is the total period of time after commencement of the interaction that the animal can choose to interact with the device. As with the previous two settings, instead of choosing a fixed duration during initialization, the device may choose a duration that varies according to a dynamic program under the control of the device controller. Another configuration made at device initialization is the configuration of the secondary reinforcement sound. This is a sound that is provided in the immediate vicinity of the primary reinforcer in order to create a psychological association within the animal of the selected secondary reinforcer and the primary reinforcer. Though the secondary reinforcer is likely to be chosen ahead of time, the system may also have a secondary reinforcement sound that is dynamically controlled or changed by the device's controller.

The critical learning component provided by this flow chart is the changing of the device's programming as soon as the device detects that the animal has made a button press. As soon as the system detects that the animal made a press, the system switches from auto-dispense, in which food is dispensed for free, to the "animal controls food access directly" programming, in which the animal must make a button press in order to receive food.

Example 9—Real-Time Animal Position Cueing

Tens of millions of pets spend their days alone at home doing very little. While the home is empty, both the entertainment system and the pet will often sit idle. Connected to many of the entertainment systems are often "gaming consoles"—devices such as the XBOX® or PLAYSTATION® that provide a powerful and flexible computing platform. The most recent versions of the XBOX® and PLAYSTATION® also provide camera-based input: their intended use is to provide humans with a body-position-based interface. Though these devices are designed for human use, they can also be used to track the location and physical configuration of any visible object.

Through the use of 3D cameras, the animal can be trained to position one of its body parts within a particular volume of space visible to a 3D camera. The device begins by first teaching the animal "come here" (see above). As soon as the animal is visible, the device estimates the location of a particular body part, for instance the animal's nose (see FIG. 19). It then calculates the error between the animal's body part and a target volume in space. If the animal's body part is within the target volume, the device rewards the animal. If the animal's body part is outside the volume, the device emits a sound modulated to correspond in near real time to the distance between the animal's nose and the target volume, thereby indicating to the animal, via this sound, the animal's body part's distance from the target volume. The procedure begins with a larger target volume that is easy to accidentally enter, thereby giving the animal an opportunity to learn which sound modulations correspond to obtaining a reward. After the animal has successfully entered the target volume, the volume can be made gradually smaller in size, thereby challenging the animal and further teaching it the correspondence between modulation of the sound and food reward.

Advantages

An advantage of the device and system described herein is its cost. In one example, a home gaming system that many households already possess can be utilized with the system and an additional component can be added, the animal interaction device, to interact with pets. It does not require a special collar, the purchase of a separate specialized computer, a purpose-specific camera system, purpose-specific speakers, tracking devices, or video monitors. Another advantage is that the system is software-driven—this permits an unlimited number of training, entertainment, monitoring, and research interaction programs. Another advantage of using advanced mass market home gaming/computer systems is that the system can be connected to the Internet. This allows rapid updating of the software that controls programs, animal monitoring, and even the opportunity for animals to interact (electronically) with other animals. Another advantage to using an internet-connected software-based device is that it can allow owners to interact with and explore alternative training programs, sharing their pet's progress with others, and discussing potential revisions to programs. Another advantage of the system's simplicity, familiar hardware, and software control, is ease-of-use—the animal owner does not need to learn to use any new hardware apart from the animal interaction device.

Computer-controlled automated home animal training devices have not yet received widespread commercial adoption, despite the existence of relevant publicly available technology proposals for more than six years. Existing inventions and approaches have to this point failed to achieve market success, and none have demonstrated flexibility or effectiveness. Those described within the prior art are both expensive and complicated. The invention described here is neither.

Operation

Initial set up: The operator (the human) would first fill the dispenser with the appropriate pet treats or food, and connect the animal interaction device to the home electrical system. The animal interaction device could be placed in any nearby animal—accessible location.

Initially, it is likely that the operator would program the animal interaction device so that the operator's own voice could give commands to the animal. When the animal interaction device prompted him or her the operator would speak the phrases requested (depending on language and operator preference) for, e.g., "come here", and any number of other instructions proper to the programs used.

The operator may also, optionally, connect the animal interaction device to the home entertainment system. When starting the system up, the operator would therefore also turn on the home's gaming and entertainment systems. This would allow the system to potentially use 3D camera sensors. In this latter case, there might also be additional calibration in for the system, during which the user would teach the system the name of different potentially relevant objects (e.g. dog toys, shoes). The system may also gather a range of views of the animal in order to acquire enough visual data in order to recognize the animal again in the future. Once the operator performed this initial set up, s/he would leave the software running, at which point it would begin to perform as an entertainment/training/monitoring/research system.

Initial Animal Orientation

After triggering the reward cue and producing a food reward, the system would attempt to attract the animal's attention. The system may use a (perhaps blinking) light, as well as creating an attractive audible sound, in order to ensure that the animal investigates the area where the food reward is. Once the animal demonstrates learning of the reward location, the training to increase the delay between the cue time and the reward provision would take place, causing the reward cue to increase in importance to the animal. If the system has a 3D camera sensor, the system may also use this opportunity to acquire additional data about the animal—for instance, how the animal moves and what it looks like.

Typical Use

Once the animal was familiar with operation of the system, the operator would start operation of the software, perhaps s/he would choose a (training/research/monitoring/entertainment) program, and could choose to watch the animal (no doubt every operator would do this at first), or choose to leave the animal with the system. No further interaction between the operator and the system, or the operator and the animal, would be required (until the operator chooses to terminate the software, perhaps in order to use the home entertainment system for another purpose).

Given that there is only the system and the animal, the first thing the system would likely do would be to try and get the animal's attention. The animal has already learned association of the reward cue with the reward. Depending on the particular configuration and availability of components within the system, the next object that might be pursued (if a 3D camera was available) would likely be to cue-and-reward the animal for arriving at, and staying in, one place in front of the system. The system may also be designed so as to make greater use of the operator within programs, thus providing additional engagement to all parties.

The system's programming would then scaffold new behaviors and skills on to the animal, increasing the animal's engagement with the system. Using techniques, perhaps ones derivative of those presented above, the system would train the animal so that the animal learned the relevance of information presented on a video screen, and so that the animal learned the relevance of information presented acoustically (via the loudspeakers) and in doing so the animal may even learn to exert some amount of control over the system itself—for instance, the system may teach the animal to use its body as a "mouse" to control which program the animal would like to engage with.

Internet Integration

The software that controls animal training/entertainment/monitoring/research programs could also provide a platform for operator-created/modifiable and shareable programs. This would allow millions of operator to share, compare, and collaborate in the development of more (and more elaborate) programs, permitting (e.g.) operators to discover new abilities that their pets might have. This might also provide a payment-based ecosystem of programs whereby the platform allows certain operator to sell animal training programs to other operators.

Research Integration

Operators might choose to allow their animals to participate in research experiments delivered via the Internet. E.g., a qualified researcher may wish to know the average working memory capacity of animals at different animal age levels. Researchers might choose to pay animal owners, or animal owners may be required to provide their animal for a certain percentage of time, or animal owners may simply opt to allow their animals to be used for (benign) experimental purposes for other kinds of rewards or simply due to generosity or curiosity.

Operator Program Creation and Modification

Software would be provided that allowed operators to modify training programs. The simple version of the program design software may resemble the "Scratch" programming environment (http://scratch.mit.edu/), but text-based program design functions would also likely be provided. Software would be completely customizable, but operators would be directed toward best practices for achieving particular goals viz. their pets.

Examples of Other Uses are Provided in Table 2:

TABLE 2

1) Animal competitions—operators could allow their pet to compete against other pets around the world, e.g.
   a) Most exercise
   b) Greatest cognitive ability
   c) Most words learned
   d) Most skills mastered
2) Monitoring—operators could view their animal, e.g.
   a) Highlights (in real time)
   b) May be alerted to particular accomplishments
3) Health tracking, e.g.
   a) Gait analysis
   b) Behavior analysis for health issues (depression, anxiety, dementia, asthma, etc.)
4) Exercise, e.g.
   a) Program could have animalrun back and forth between spots on the floor
5) Could be integrated with one or more lasers to present targets on the ground.
6) Different kinds of reward devices could be used to allow use of system to train/monitor/entertain/study birds
7) Could include use and control of an aversive feedback dog collar
8) May include use of aversive sounds, perhaps at high pitch, using the home entertainment system's speakers or another device
9) May also include the provision ("upgrades") of special--/use hardware, e.g.
   a) Electrified/aversive or positive reward dog collars.
10) Therapeutic, e.g., could be used to prevent anxiety problems by providing images/sounds of operator occasionally, or when requested by animal.
11) Could include use of animatronic "petting" device.
12) May include device that emits different animal--/relevant smells.
13) Multiple video displays.
14) Rewarding device may have a two-way mode of communication with the computer, e.g.,
   a) Provide information regarding treat/food reservoir status
   b) Provide information confirming animal ate food
15) Rewarding device may use a number of different methods to attract animal's attention—especially helpful during initial period, e.g.:
   a) Light
      i) flashing
   b) Sound, e.g.:
      i) Simulated scratching
      ii) Simulated operator's voice
      iii) Treats falling and hitting a surface
16) Operators could be presented every day with an animal learning highlights reel, e.g.,
   a) "Highlights reels" could be shared with others online
17) Multiple animals could be trained to engage in activities with each other
18) Animal could be taught to avoid particular pieces of furniture.
19) System might be integrated with, e.g.,
   a) Google ™ Glass ™ to allow operators potentially constant interaction with their pet
20) System could make use of a full day of recorded information about the operator (e.g. voice signature) in order to generate training stimuli.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

FIGURE LEGEND

100: Animal interaction device
102: Device housing
106: Animal
110,112,114: Programmatically illuminated interaction touch sensors/indicators
104: Cover of food hopper
140: Food presentation area
142: Microphone
143: Speaker
144: Camera
145: Context cue light
146: Food
148: Food tray
150: Presentation platform
400: Device platform
410: Device legs
420: Conveyor angle guide
422: Food conveyor channel
424: Food hopper
426: Conveyor motor assembly
428: Conveyor pivot
430: Conveyor/platform support frame (also 810, 812)
510: Conveyor motor
512: Spiral conveyor coil
518: Food drop detector
520: Presence-of-food detector
522: Conveyor assembly
810: Conveyor/platform support frame (also 430, 812)
812: Conveyor/platform support frame (also 430, 810)
814: Presentation platform motor
902: Presentation platform friction drive assembly
905: Presentation platform motor wheel
910: Presentation platform friction drive wheel
1100 Conveyor motor shaft
1300 Animal interaction system
1302 Animal
1304 Stimuli 1306 Animal condition
1308 Reinforcement
1310 Animal interaction device
1312 Indicators
1313 Controller presents stimuli via indicators
1314 Sensors
1315 Controller senses via sensors
1316 Food access component
1317 Controller controls presentation of reinforcement
1320 Controller
1322 Animal interaction algorithm
1324 Transmit data to remote computer
1326 Update animal interaction algorithm
1330 Internet communication
1350 Other animal interaction devices
1360 Network of remote computer(s)
1362 Data storage
1364 Data analysis
1366 Instructions for updating animal interaction device
1380 Operator interface
1382 Data and analysis visualization
1384 Operator command interface
1386 Operator data input

What is claimed is:

1. A system for automatically interacting with an animal, the system comprising: at least one animal interaction device, each animal interaction device comprising an initial interaction algorithm to automatically interact with the animal, the initial interaction algorithm comprising device instructions for:
    presenting stimuli;
    recording one or more variables including at least the animal condition;
    controlling timing and duration of reinforcement;
    transmitting the one or more variables recorded to at least one remote computer; and
    receiving from the at least one remote computer, a modified interaction algorithm to replace the initial interaction algorithm, wherein the modified interaction algorithm is based at least in part on the one or more variables recorded and modifies the device instructions for presenting stimuli or controlling the timing and the duration of reinforcement.

2. The system of claim 1, wherein the animal interaction device comprises a food access component which allows and disallows access to at least a portion of the food dependent upon the animal condition sensed when the animal is in proximity to the device.

3. The system of claim 1, wherein the interaction algorithm is selected from a group consisting of training, modifying behavior, and modifying the animal condition.

4. The system of claim 1, wherein the reinforcement is one of positive or negative reinforcement.

5. The system of claim 4, wherein the positive or negative reinforcement is removed after a period of time.

6. The system of claim 1, wherein the one or more variables are recorded continuously or intermittently, and data from the continuous or intermittent recordings are segregated and inform the modification of the initial or modified interaction algorithm.

7. The system of claim 1, wherein the initial interaction algorithm is downloaded upon starting the device.

8. The system of claim 1, wherein the interaction algorithm is housed on the at least one remote computer, and instructs the at least one animal interaction device to perform the instructions.

9. The system of claim 1, wherein the modification to the initial interaction algorithm at the at least one remote computer is based at least in part on data from at least one additional animal interaction device associated with a different animal.

10. A method for modifying the function of an animal interaction device, the method comprising:
    receiving, at a remote computing device, data from an animal interaction device, the data comprising at least information about an animal's condition and how the animal interacted with the animal interaction device while the animal interaction device was controlled by a first algorithm, wherein the first algorithm contains instructions for presenting stimuli and controlling timing and duration of reinforcement;
    modifying the first algorithm based at least in part on the data; and
    transmitting the modified algorithm to the animal interaction device, wherein the modified algorithm changes the instructions for presenting stimuli to the animal and the timing and duration of reinforcement.

11. The method of claim 10, wherein the reinforcement is one of positive or negative reinforcement and the positive or negative reinforcement is removed after a set duration of time.

12. The method of claim 10, wherein the modified algorithm is based at least in part on data about interaction of other animals with other animal interaction devices.

13. The method of claim 12, wherein the stimuli is presented to improve the ability of the animal interaction device to interact with the animal.

14. A method for controlling the function of an animal interaction device, the method comprising:
    receiving, at a computing device, data from an animal interaction device, the data comprising at least information about an animal's condition;
    determining how the animal is likely to interact with the animal interaction device based at least in part on the data and how other animals sharing at least one similarity in animal condition data have interacted with other animal interaction devices;
    generating control instructions for the animal interaction device based at least in part on how the animal is likely to interact with the animal interaction device; and
    transmitting the control instructions to the animal interaction device.

15. The method of claim 14, wherein the control instructions generated are based at least in part on a prediction of how those instructions will alter the likelihood that the animal will achieve a specified goal state.

16. The method of claim 14, wherein the control instructions generated are based at least in part on a prediction of how those instructions will maximize the likelihood that the animal will achieve a specified goal state.

17. The method of claim 14, wherein the control instructions generated are based at least in part on cognitive models.

18. The method of claim 14, wherein the control instructions generated are based at least in part on animal breed.

19. The method of claim 14, wherein the control instructions are modified on a continuous basis.

20. The method of claim 14, wherein the control instructions are modified on an intermittent basis.

* * * * *